(12) United States Patent
Grunewald et al.

(10) Patent No.: US 8,900,228 B2
(45) Date of Patent: Dec. 2, 2014

(54) CATHETER ADAPTED FOR DIRECT TISSUE CONTACT AND PRESSURE SENSING

(75) Inventors: Debby Grunewald, Los Angeles, CA (US); Meir Bar-Tal, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 373 days.

(21) Appl. No.: 13/463,330

(22) Filed: May 3, 2012

(65) Prior Publication Data

US 2013/0123775 A1    May 16, 2013

Related U.S. Application Data

(63) Continuation-in-part of application No. 13/224,291, filed on Sep. 1, 2011.

(51) Int. Cl.
| | | |
|---|---|---|
| A61B 18/18 | (2006.01) | |
| A61B 18/14 | (2006.01) | |
| A61B 18/00 | (2006.01) | |
| A61B 19/00 | (2006.01) | |

(52) U.S. Cl.
CPC ... A61B 18/1492 (2013.01); *A61B 2018/00029* (2013.01); *A61B 2019/465* (2013.01); *A61B 2218/002* (2013.01); *A61B 2018/00875* (2013.01); *A61B 2018/00791* (2013.01); *A61B 2019/5251* (2013.01); *A61B 2018/00821* (2013.01); *A61B 2018/00797* (2013.01)
USPC .......................................................... 606/41

(58) Field of Classification Search
CPC ............... A61B 18/14; A61B 18/1492; A61B 2018/00357; A61B 2018/00577
USPC .......................................................... 606/41
See application file for complete search history.

(56) References Cited

U.S. PATENT DOCUMENTS

| | | | |
|---|---|---|---|
| 5,688,267 | A | 11/1997 | Panescu et al. |
| 5,755,715 | A | 5/1998 | Stern et al. |
| 5,853,409 | A | 12/1998 | Swanson et al. |
| 5,964,757 | A | 10/1999 | Ponzi |
| 6,030,379 | A | 2/2000 | Panescu et al. |

(Continued)

FOREIGN PATENT DOCUMENTS

| | | |
|---|---|---|
| EP | 1922991 A1 | 5/2008 |
| EP | 2047797 A2 | 4/2009 |

(Continued)

OTHER PUBLICATIONS

International Search Report and Written Opinion of the International Searching Authority, dated Oct. 23, 2013, issued in PCT/US2013/039477.

(Continued)

*Primary Examiner* — Robert N Wieland

(57) ABSTRACT

An irrigated ablation catheter adapted for direct tissue contact has micro-elements that provide more accurate sensing of tissue, including thermal and electrical properties for temperature and impedance and intracardiac ECG measurements. A pressure sensing assembly adds the ability to measure the force at the tip of the catheter as well as to have the micro-elements for accurately sensing tissue parameters. A system uses signals from the micro-elements (impedance, temperature, and ECG signals) as well as the measure of force or pressure at the tip electrode order to provide the operator with a means to control lesion depth, size, transmurality and to ablate tissue until successful treatment of an arrhythmia is achieved.

38 Claims, 23 Drawing Sheets

(56) References Cited

U.S. PATENT DOCUMENTS

| | | |
|---|---|---|
| 6,063,078 A | 5/2000 | Wittkampf |
| 6,176,857 B1 | 1/2001 | Ashley |
| 6,371,955 B1 | 4/2002 | Fuimaono et al. |
| 6,468,260 B1 | 10/2002 | Bumbalough et al. |
| 6,500,167 B1 | 12/2002 | Webster, Jr. |
| 6,500,172 B1 | 12/2002 | Panescu et al. |
| 6,522,933 B2 | 2/2003 | Nguyen |
| 6,611,699 B2 | 8/2003 | Messing |
| 6,616,657 B2 | 9/2003 | Simpson et al. |
| 6,638,275 B1 | 10/2003 | McGaffigan et al. |
| 6,689,127 B1 | 2/2004 | Gough et al. |
| 7,047,068 B2 | 5/2006 | Haissaguerre |
| 7,094,215 B2 | 8/2006 | Davison et al. |
| 2003/0004506 A1 | 1/2003 | Messing |
| 2007/0287998 A1 | 12/2007 | Sharareh et al. |
| 2009/0138007 A1 | 5/2009 | Govari et al. |
| 2010/0168557 A1* | 7/2010 | Deno et al. ............ 600/424 |
| 2010/0331658 A1 | 12/2010 | Kim et al. |
| 2011/0224573 A1 | 9/2011 | Bar-Tal et al. |
| 2011/0224667 A1 | 9/2011 | Koblish et al. |
| 2012/0143088 A1 | 6/2012 | Schultz |

FOREIGN PATENT DOCUMENTS

| | | |
|---|---|---|
| EP | 2062545 A2 | 5/2009 |
| EP | 2327365 A1 | 6/2011 |
| EP | 2347726 A2 | 7/2011 |
| EP | 2564801 A1 | 3/2013 |
| WO | WO 93/08755 A1 | 5/1993 |
| WO | WO 97/33524 A1 | 9/1997 |
| WO | WO 99/25260 A1 | 5/1999 |
| WO | WO 2008/118992 A1 | 10/2008 |

OTHER PUBLICATIONS

Extended European Search Report dated Nov. 16, 2012 for EP Application No. 12182618.4.

* cited by examiner

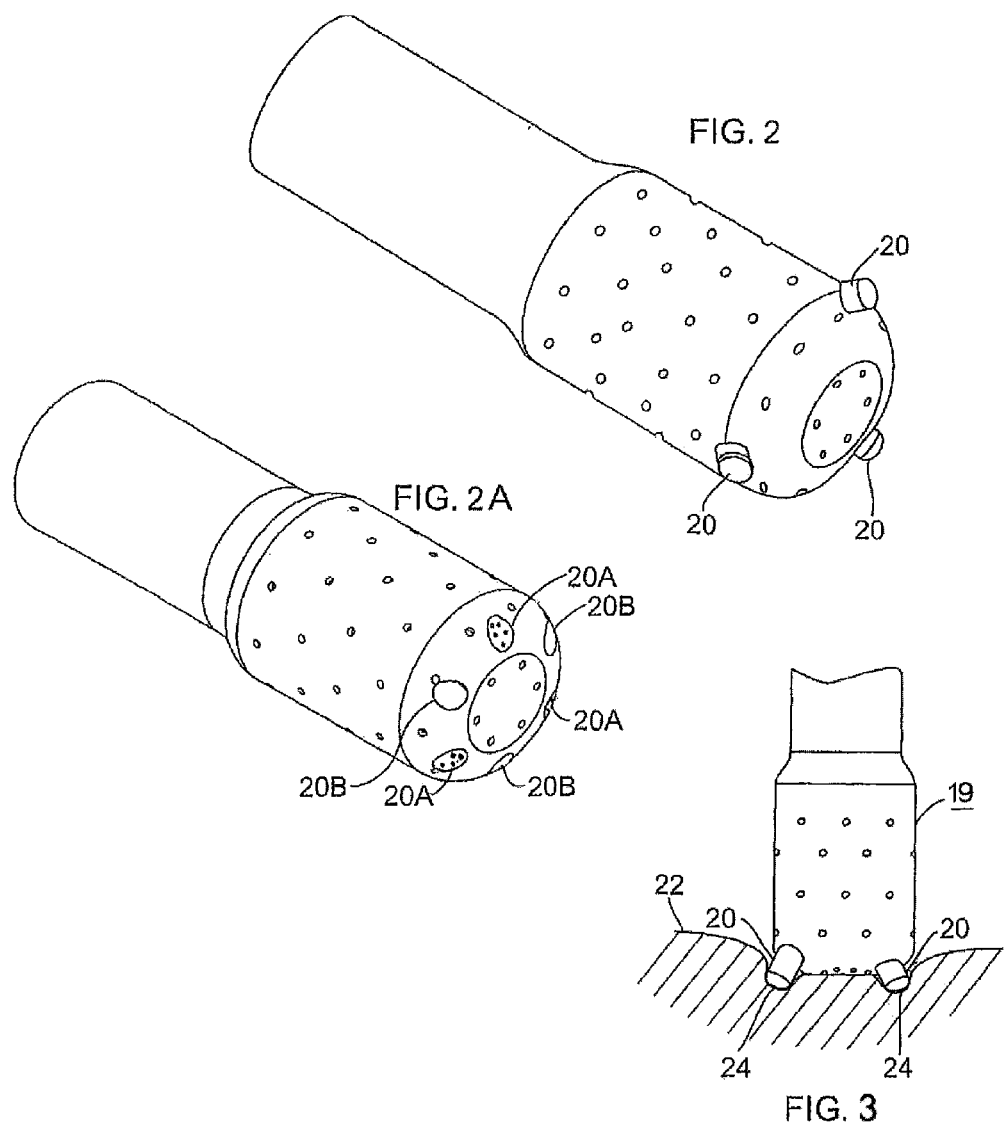

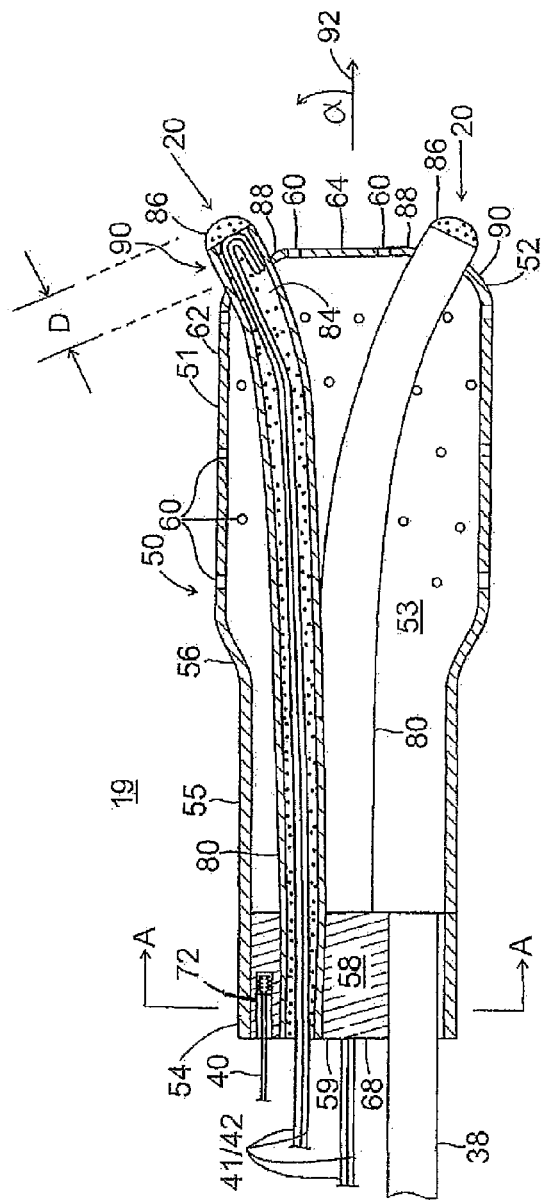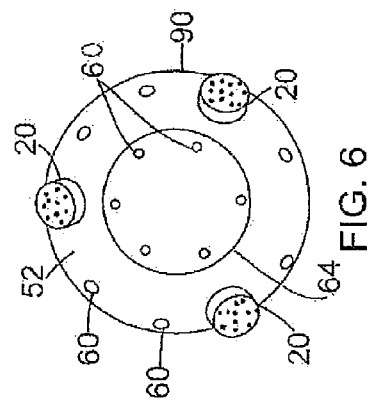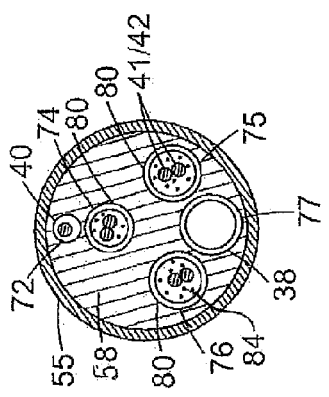

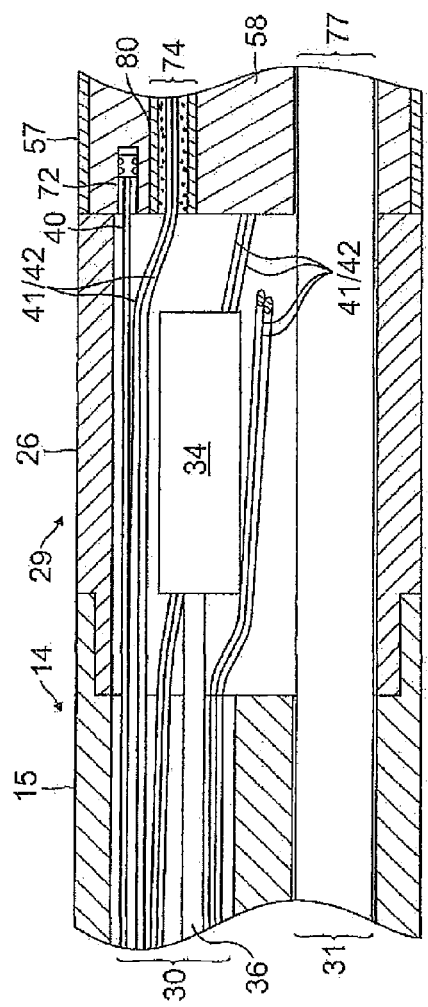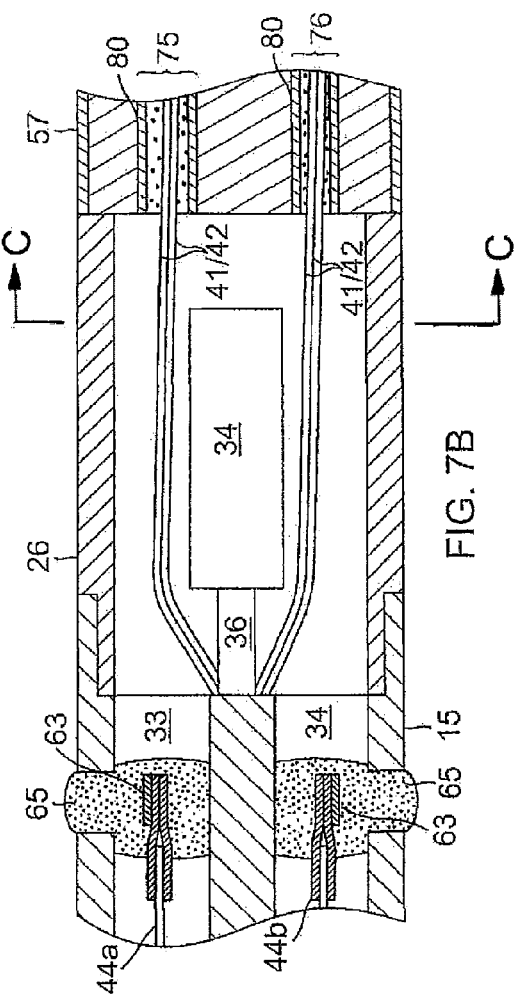
FIG. 7A
FIG. 7B

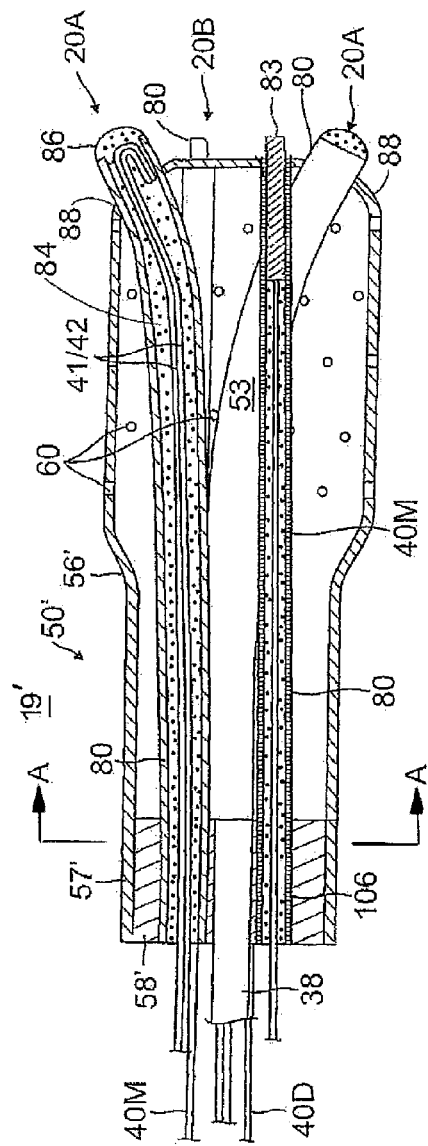
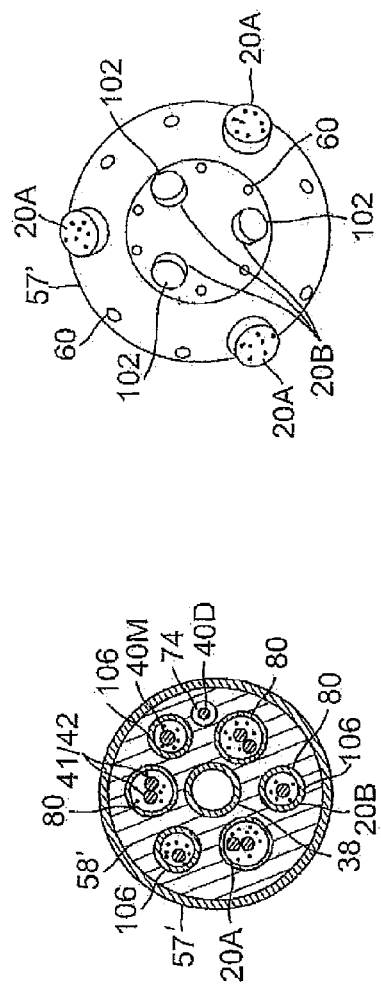
FIG. 9
FIG. 9A
FIG. 11

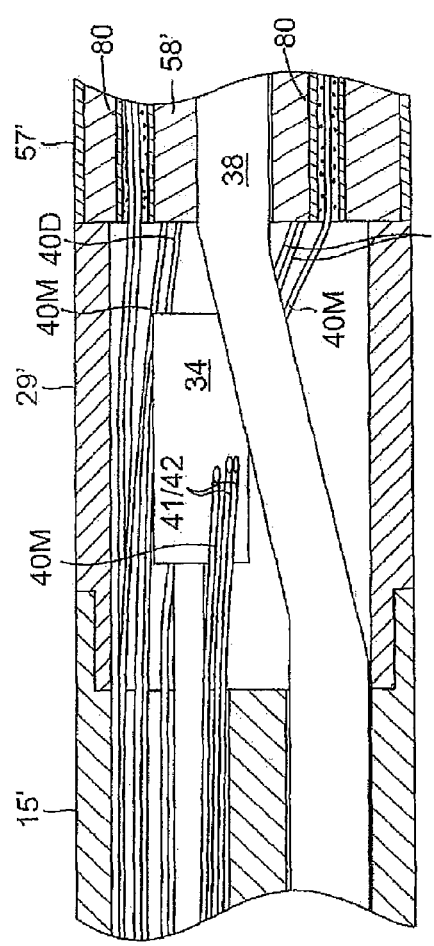
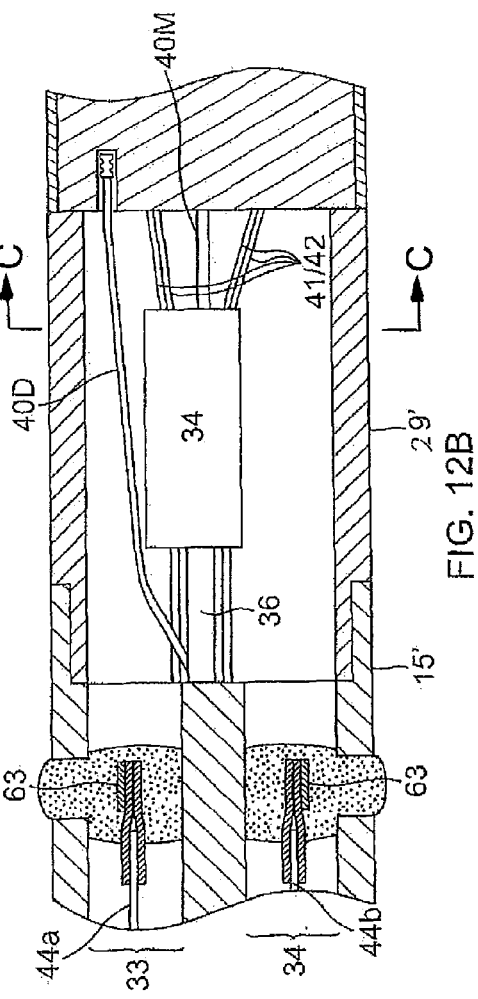

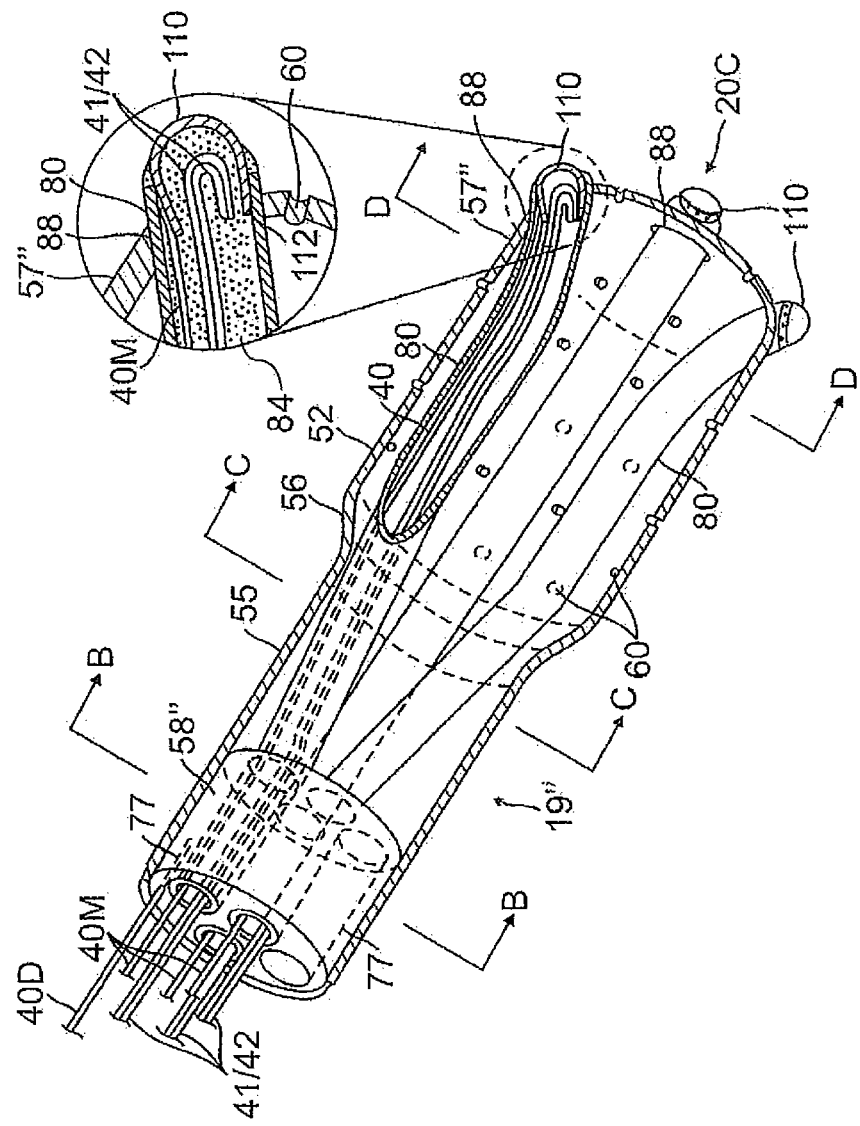

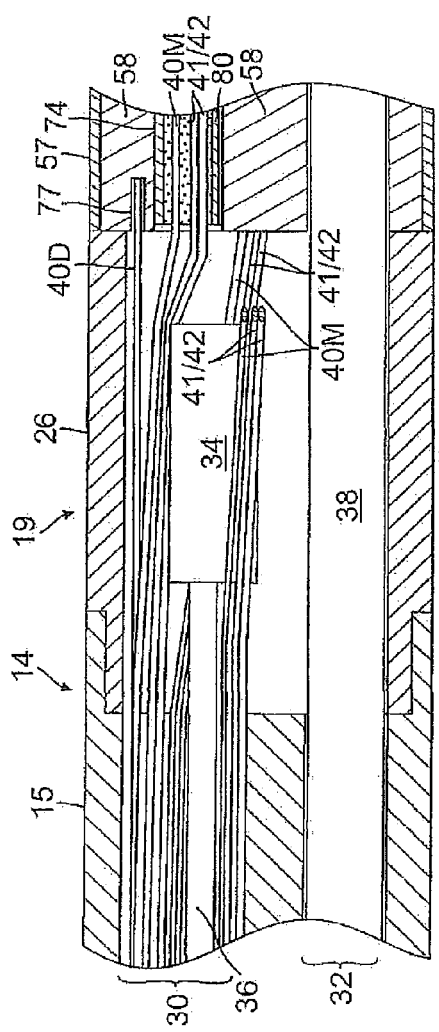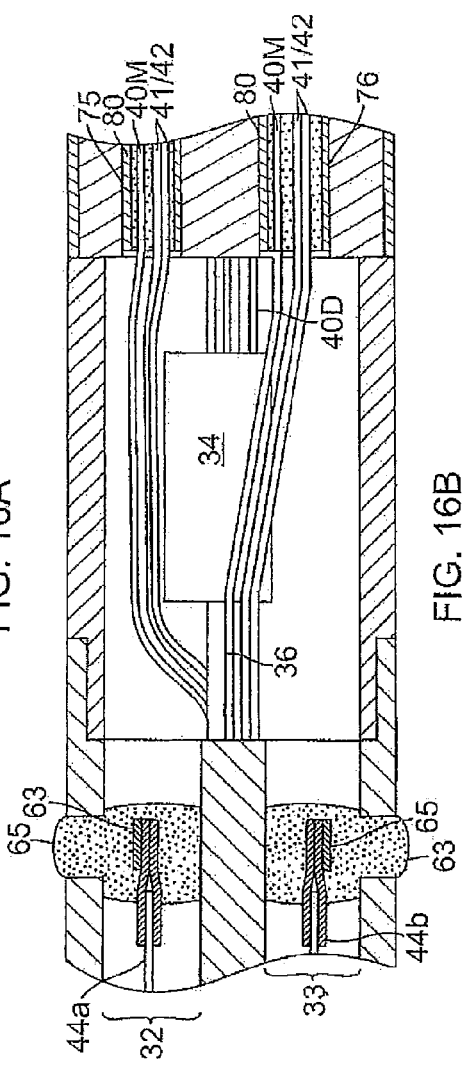
FIG. 16A
FIG. 16B

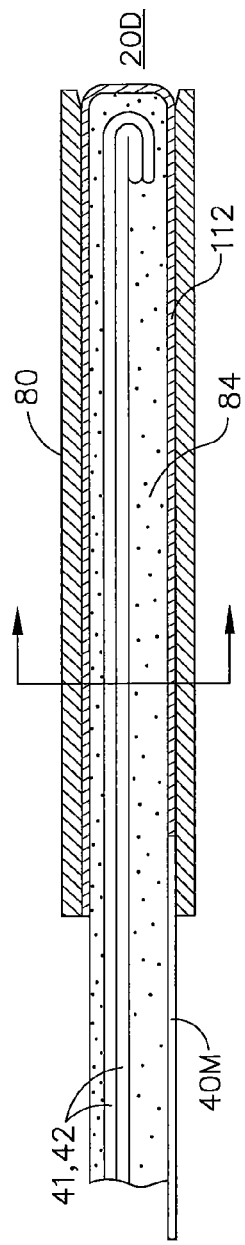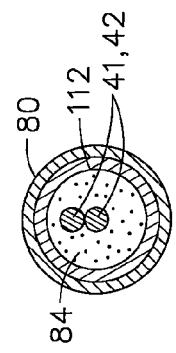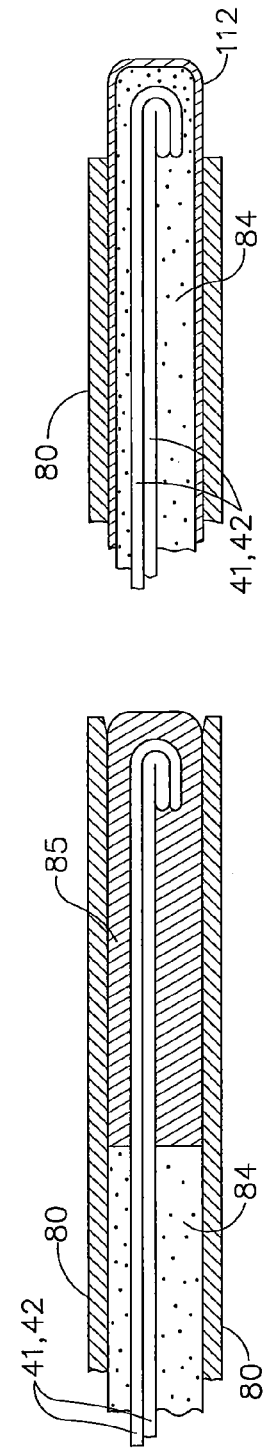

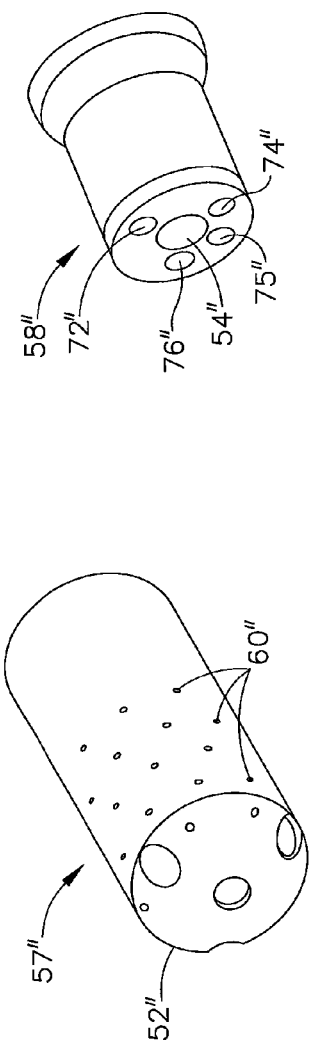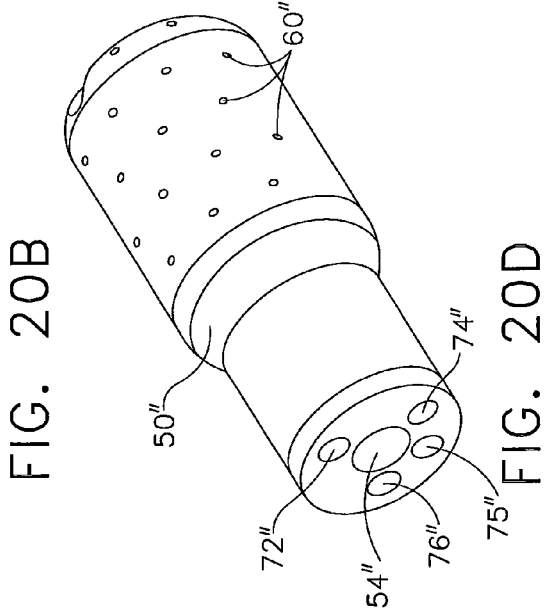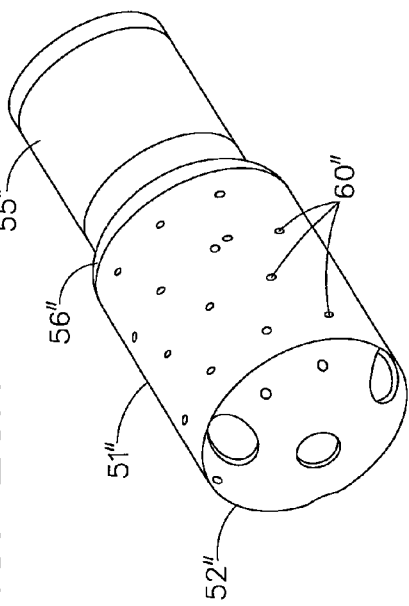

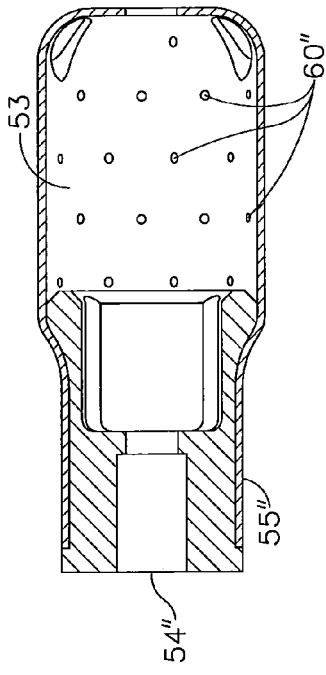
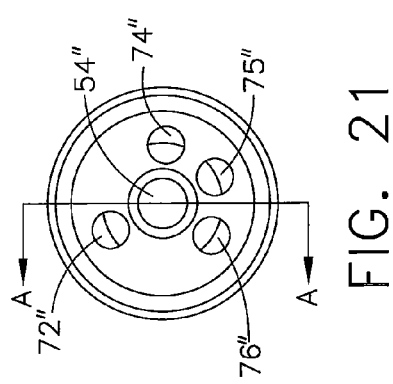
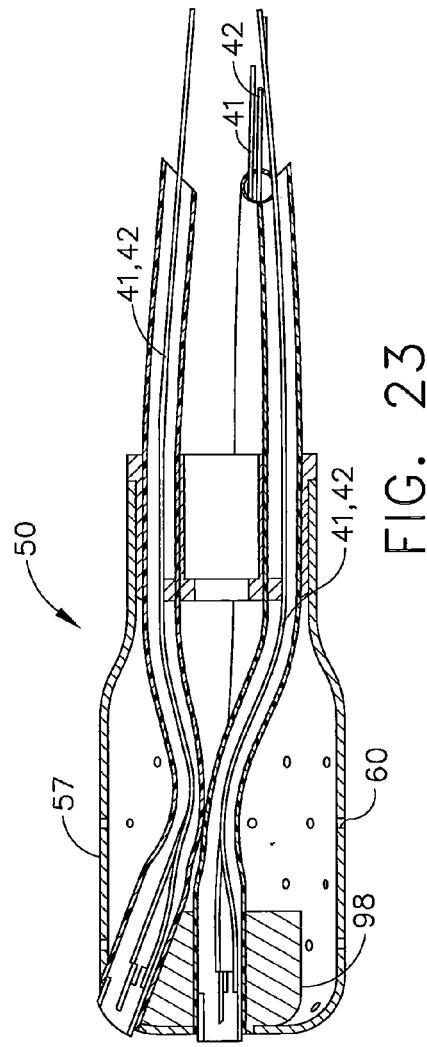

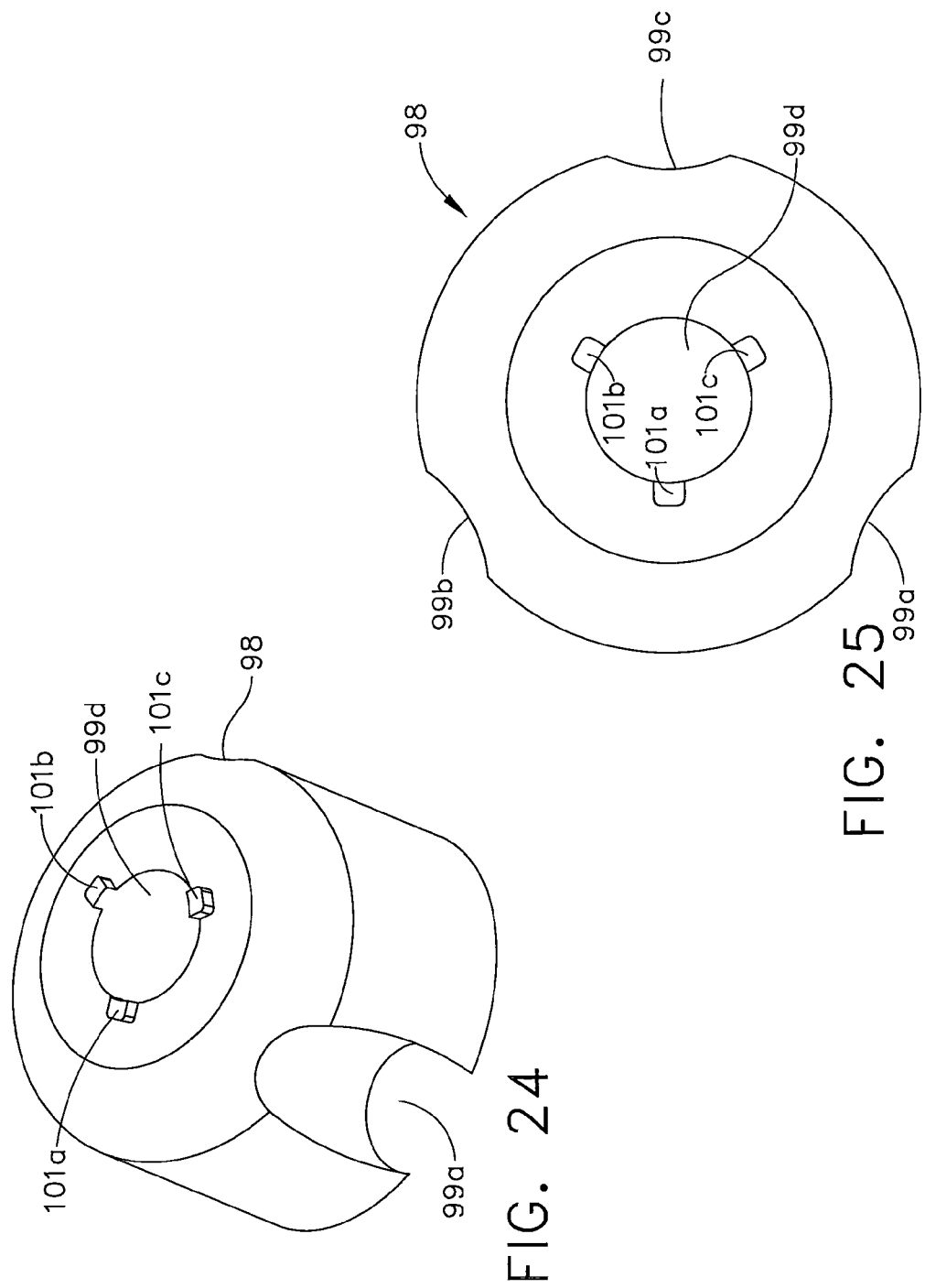

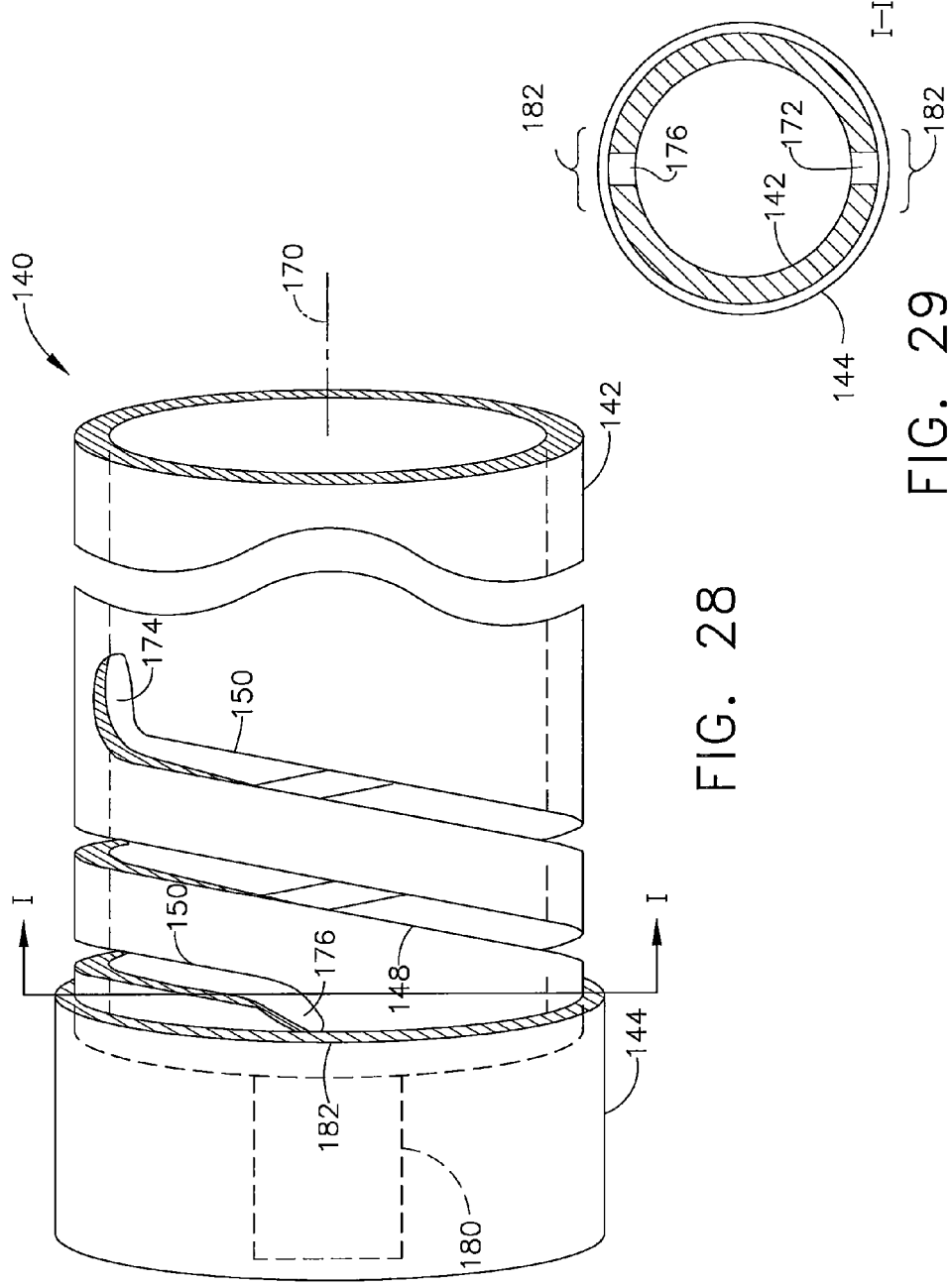

CATHETER ADAPTED FOR DIRECT TISSUE CONTACT AND PRESSURE SENSING

CROSS-REFERENCE TO RELATED APPLICATION

This application is a continuation-in-part of U.S. patent application Ser. No. 13/224,291, filed 1 Sep. 2011, which is incorporated herein by reference.

FIELD OF INVENTION

This invention relates generally to methods and devices for invasive medical treatment, and specifically to catheters, in particular, irrigated ablation catheters. More particularly, this invention relates to irrigated ablation catheters having micro-elements that provide accurate sensing of tissue, thermal and electrical properties for temperature and impedance measurements as well as a pressure-sensing element which elements can be used in an ablation system for lesion assessment.

BACKGROUND

Ablation of myocardial tissue is well known as a treatment for cardiac arrhythmias. In radio-frequency (RF) ablation, for example, a catheter is inserted into the heart and brought into contact with tissue at a target location. RF energy is then applied through electrodes on the catheter in order to create a lesion for the purpose of breaking arrhythmogenic current paths in the tissue.

Irrigated catheters are now commonly used in ablation procedures. Irrigation provides many benefits including cooling of the electrode and tissue which prevents overheating of tissue that can otherwise cause the formation of char and coagulum and even steam pops. However, because tissue temperature is assessed during an ablation procedure to avoid such adverse occurrences, it is important that the temperature sensed accurately reflects the real temperature of the tissue and not merely the surface temperature of the tissue which can be biased by the cooling irrigation fluid from the catheter. Moreover, deeper tissue contact in general provides more accurate thermal and electrical readings, including improved impedance measurements for purposes, including a determination of lesion size, depth and transmurality.

Accordingly, there is a desire for an irrigated ablation catheter with a distal end that can better probe tissue without significantly damaging or breaching the tissue, for more accurate measurements, including temperature sensing and impedance measurements.

Additionally, excessive pressure at the tip of the irrigated ablation, however, may cause undesired damage to the tissue, particularly to heart tissue and may even perforate the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue

SUMMARY OF THE INVENTION

The present invention is directed to an irrigated ablation catheter adapted for direct tissue contact by means of micro-elements (or micro-sensing members) that provide more accurate sensing of tissue, including thermal and electrical properties for temperature, impedance and ECG measurements.

The present invention is also directed to an irrigated ablation catheter that is adapted for direct tissue contact with pressure-sensing elements that provide an indication of the pressure exerted by the catheter on the tissue at the ablation element.

In one embodiment, the catheter has an elongated body and a distal electrode assembly that has an electrode having a shell configured with an inner fluid chamber. The shell has a wall with at least one aperture formed on the distal portion of the shell which receives a distal end of a micro-element extending through the inner chamber. The distal end of the micro-element extends to at least through the aperture, if not also outside of the outer surface of the wall such that there is an exposed portion adapted to probe the tissue being ablated.

In a more detailed embodiment, the micro-element can be configured as a micro-temperature sensor or a micro-electrode, or a micro-element with both capabilities and functions. The micro-element has a guide tube adapted to protect the components in its central lumen against exposure to fluid and trauma, but is sufficiently flexible to adapt to the complex and small confines inside a hollow electrode that is adapted to receive irrigation fluid and pass the fluid outside of the electrode through irrigation apertures. For temperature sensing function, the micro-element includes a pair of temperature sensing wires (e.g., thermistor wires) encased in a suitable sealant. For electrical sensing function, including impedance sensing, the micro-element carries a micro-electrode member configured for direct tissue contact, and a lead wire. For both temperature sensing and electrical sensing functions, the dual-functioning micro-element carries a pair of thermistor wires, a micro-electrode member and a lead wire. The micro-electrode member can be a discrete structure from the thermistor wires, or an electrically-conductive coating applied to the wires.

In a more detailed embodiment, the distal electrode assembly include a plurality of micro-elements whose distal ends are arranged in a radial pattern along a circumference of the distal portion of the shell electrode. Exposed distal ends of the micro-elements extend at an angle relative to the longitudinal axis of the shell electrode. The angle may have at least a distal component, if not also a radial component, as a distal end of a catheter often does not approach and make tissue contact with a direct "on-axis" approach.

Also, the plurality of micro-electrodes can include one group of micro-thermistors and another group of micro-electrodes, each group being arranged on the same circumference at the distal end of the shell electrode, interspersed with each other, or on a larger circumference and a smaller circumference, respectively.

Furthermore, the exposed portion of a micro-element can range between about 0.2 mm and 1.0 mm, preferably between about 0.3 mm and 0.6 mm, and more preferably about 0.5 mm. Each micro-element may have a diameter ranging between about 0.01 inch to 0.03 inch, preferably about 0.0135 inch.

In a further embodiment of the invention the elongated catheter body has a distal end for insertion into a body cavity of a patient, and a distal tip, which is disposed at the distal end of the elongated catheter body and is configured to be brought into contact with tissue in the body cavity. The catheter also includes a coupling member, which couples the distal tip to the distal end of the elongated catheter body and which includes a tubular piece of an elastic material having a plurality of intertwined helical cuts therethrough along a portion of a length of the piece. A position sensor is located within the tubular piece. The position sensor is be configured to sense a position of the distal tip relative to the distal end of the elongated catheter body, the position changing in response to deformation of the coupling member. The position sensor is configured to generate a signal in response to a magnetic field, and the signal is indicative of a position of the distal tip. The probe may include a magnetic field generator within the tubular part for generating the magnetic field.

Typically, the elongated catheter body, the distal tip and the coupling member are configured for insertion through a blood vessel into a heart of a patient.

There is also provided, a method and system for performing a medical procedure, including inserting a catheter into a body cavity of patient, which catheter includes an elongated catheter body and a distal tip, which is disposed at a distal end of the elongated catheter body, micro-elements for direct tissue contact and a coupling member, which couples the distal tip to the distal end of the elongated catheter body and consists of a tubular piece of an elastic material having a plurality of helical cuts therethrough along a portion of a length of the piece, and bringing the distal tip into contact with tissue in the body cavity. Typically, the method includes ablating the tissue with which the distal tip is in contact while measuring the temperature, impedance and electrogram (ECG) activity at the tip using the micro-elements and the pressure at the tip using the pressure-sensing element. These measurements are used by the system and the electrophysiologist to determine lesion size, depth and transmurality and whether the lesion is successful in blocking the arrhythmogenic current paths in the tissue.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 2 is a perspective view of an electrode assembly in accordance with an embodiment of the present invention.

FIG. 2A is a perspective view of an electrode assembly in accordance with another embodiment of the present invention.

FIG. 3. is a side elevational view of the electrode assembly of FIG. 2 in direct contact with tissue.

FIG. 5 is a side-cross-sectional view of the electrode assembly of FIG. 2.

FIG. 5A is an end-cross-sectional view of the electrode assembly of FIG. 5, taken along line A-A.

FIG. 6 is an end view of the electrode assembly of FIG. 2.

FIG. 7A is a side cross-sectional view of a portion of the catheter of FIG. 1, including a connecting portion, taken along one diameter.

FIG. 7B is a side cross-sectional view of the portion of the catheter of FIG. 7A, taken along another diameter.

FIG. 9 is a side-cross-sectional view of the electrode assembly of FIG. 8.

FIG. 9A is an end cross-sectional view of the electrode assembly of FIG. 9, taken along line A-A.

FIG. 11 is an end view of the electrode assembly of FIG. 8.

FIG. 12A is a side cross-sectional view of an embodiment of a connection portion and an intermediate deflectable section suitable for the electrode assembly of FIG. 8, taken along one diameter.

FIG. 12B is a side cross-sectional view of an embodiment of a connection portion and an intermediate deflectable section suitable for the electrode assembly of FIG. 8, taken along another diameter.

FIG. 15 is a side cross-sectional view of the electrode assembly of FIG. 14.

FIG. 15A is an enlarged view of a distal end of a micro-element of FIG. 15.

FIG. 16A is a side cross-sectional view of an embodiment of a connection portion and an intermediate deflectable section suitable for the electrode assembly of FIG. 15, taken along one diameter.

FIG. 16B is a side cross-sectional view of an embodiment of a connection portion and an intermediate deflectable section suitable for the electrode assembly of FIG. 15, taken along another diameter.

FIG. 18 is a side cross-sectional view of a micro-element in accordance with an embodiment of the present invention.

FIG. 18A is an end cross-sectional view of the micro-element of FIG. 18, taken along line A-A.

FIG. 18B is a side cross-sectional view of a micro-element in accordance with another embodiment of the present invention.

FIG. 19 is a side cross-sectional view of a micro-thermistor in accordance with another embodiment of the present invention.

FIGS. 20A, 20B, 20C and 20D are perspective views of another embodiment of the present invention representing the unswaged thin shell, the plug and the swaged thin shell over the plug respectively.

FIG. 21 is an end view of the swaged thin shell over the plug shown in FIGS. 20C and 20D taken from the proximal end.

FIG. 22 is a cross-sectional view of the swaged thin shell over the plug of FIG. 21 through lines A-A.

FIG. 23 is a cross-sectional view of another embodiment of the present invention having a plastic insert in the thin shell.

FIG. 24 is a perspective view of the plastic insert of the embodiment shown in FIG. 23.

FIG. 25 is an end view of the distal end of the plastic insert of the embodiment shown in FIG. 23

FIG. 28 is schematic perspective view of the coupling member, according to an embodiment of the present invention FIG. 29 a schematic section of the coupling member, according to an embodiment of the present invention.

DETAILED DESCRIPTION OF THE INVENTION

Figure 1:
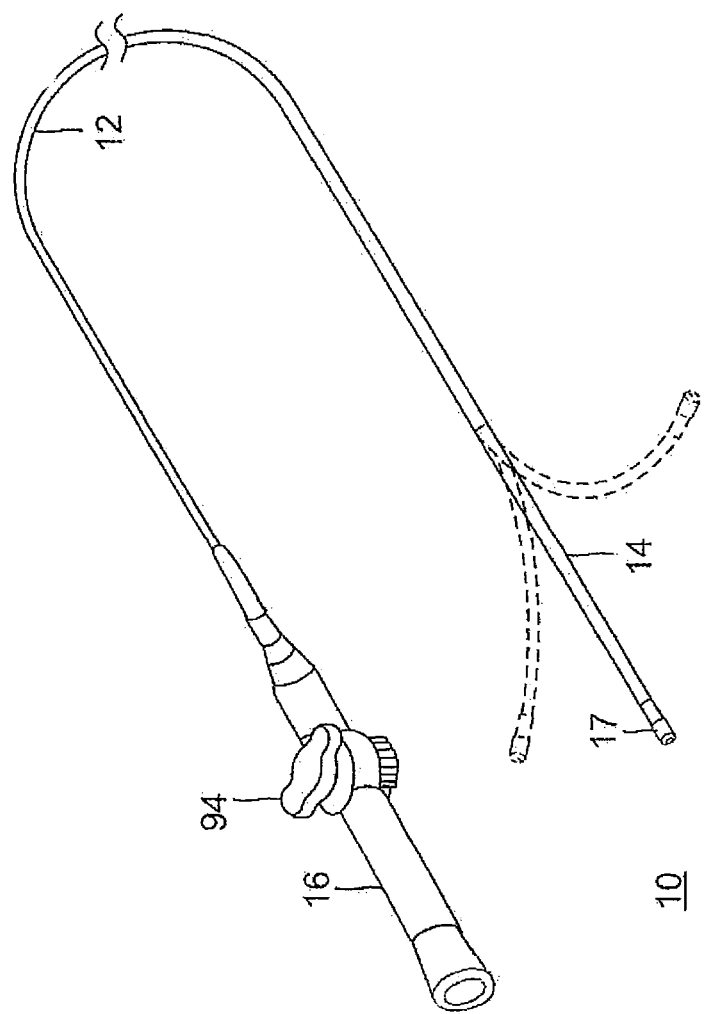
FIG. 1 is a perspective view of a catheter in accordance with an embodiment of the present invention.

As illustrated in FIGS. 1, 2 and 3, the present invention includes a steerable catheter 10 with a distal tip section 17 that includes an electrode assembly 19 and at least one micro-element 20 having an atraumatic distal end adapted for direct contact with target tissue 22. As illustrated in FIGS. 2 and 3, the distal end may have an external portion that is exposed and protrudes distally of the electrode assembly 19 to deform tissue and create micro-depression 24 where the external portion depresses and/or sinks into the micro-depression so as to be surrounded and buried in the tissue without penetrating, piercing or otherwise breaching the tissue. Alternatively, the distal end of the micro-element 20 may be flush with an outer surface of the electrode assembly 19, as illustrated in FIG. 2A. In either embodiment, each micro-element may be configured as a temperature sensor, e.g., thermistor, thermocouple, fluoroptic probe, and the like, or electrode for sensing and/or ablation. Each micro-element can also be configured to provide all afore-mentioned functions, as desired.

Referring to FIG. 1, the catheter 10 according to the disclosed embodiments comprises an elongated body that may include an insertion shaft or catheter body 12 having a longitudinal axis, and an intermediate section 14 distal of the catheter body that can be uni- or bi-directionally deflectable off-axis from the catheter body. Distal of the intermediate section 14 is the electrode assembly 19 carrying at least one micro-element. Proximal of the catheter body is a control handle 16 that allows an operator to maneuver the catheter, including deflection of the intermediate section 14.

Figure 4A:
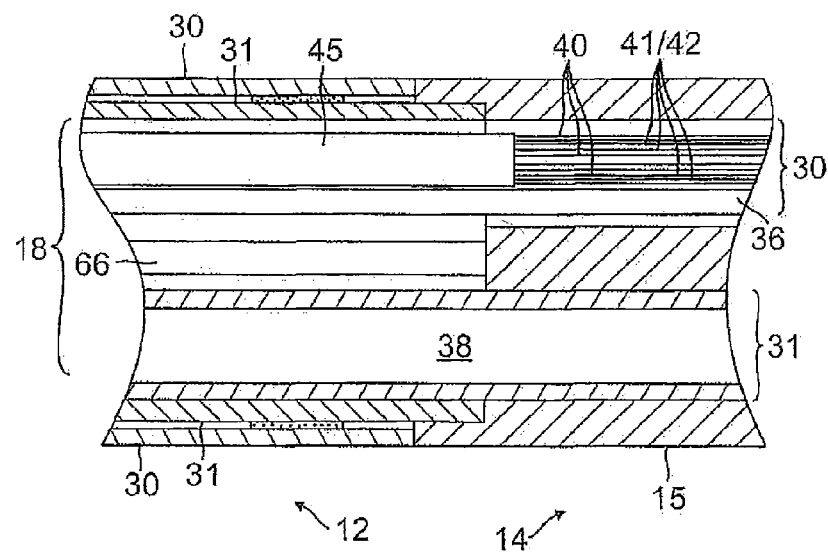
FIG. 4A is a side cross-sectional view of a portion of the catheter of FIG. 1, including a junction of a catheter body and an intermediate deflectable section, taken along one diameter.
Figure 4B:
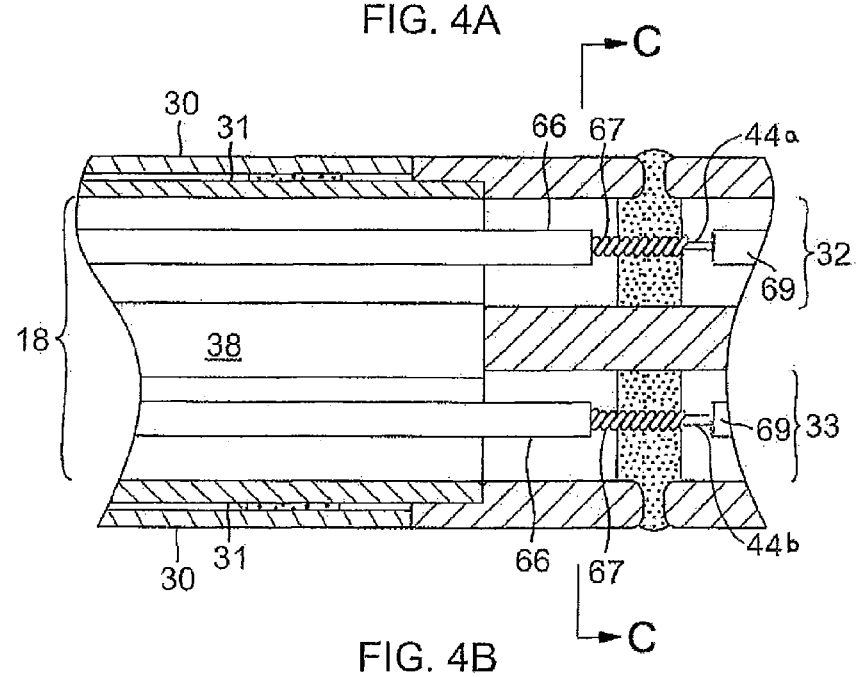
FIG. 4B is a side cross-sectional view of a portion of the catheter of FIG. 1, including a junction of a catheter body and an intermediate deflectable section, taken along another diameter.

In the depicted embodiment of FIGS. 4A and 4B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 30 made of polyurethane or PEBAX. The outer wall 30 comprises an imbedded braided mesh of stainless steel or the like, as is generally known in the art, to increase torsional stiffness of the catheter body 12 so that, when the control handle 16 is rotated, the intermediate section 14 and distal section 17 will rotate in a corresponding manner.

The outer diameter of the catheter body 12 is not critical, but is preferably no more than about 8 french, more preferably 7 french. Likewise the thickness of the outer wall 30 is not critical, but is thin enough so that the central lumen 18 can accommodate any desired wires, cables and/or tubes. The inner surface of the outer wall 30 is lined with a stiffening tube 31 to provide improved torsional stability. The outer diameter of the stiffening tube 31 is about the same as or slightly smaller than the inner diameter of the outer wall 30. The stiffening tube 31 can be made of any suitable material, such as polyimide, which provides very good stiffness and does not soften at body temperature.

Figure 4C:
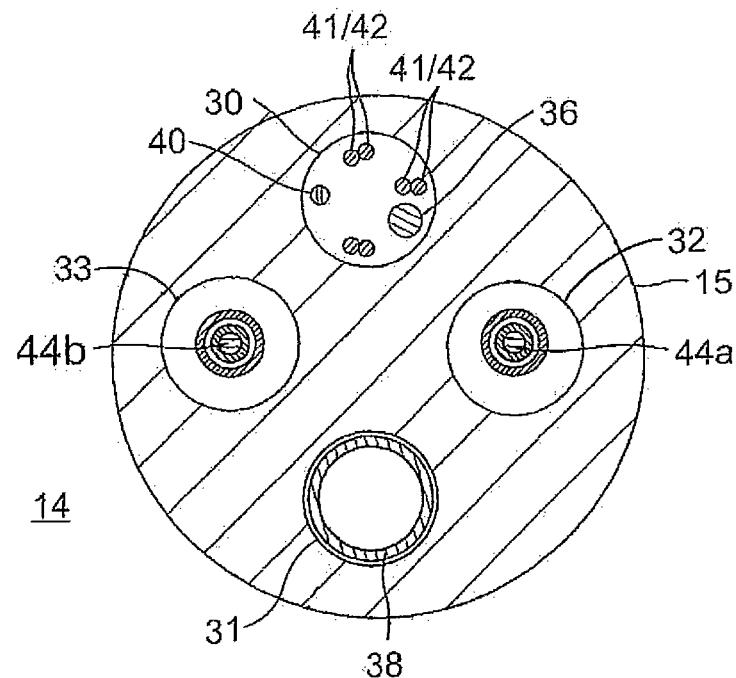
FIG. 4C is an end cross-sectional view of the portion of the catheter of FIG. 4B, taken along line C-C.

As illustrated in FIGS. 4A, 4B and 4C, the deflectable intermediate section 14 comprises a short section of tubing 15 having multiple lumens, each occupied by the various components extending through the intermediate section. In the illustrated embodiment, there are four lumens 30, 31, 32 and 33 as best seen in FIG. 4C. Passing through a first lumen 30 are lead wire 40 for the electrode assembly 19, a thermocouple pair 41/42 for each micro-element adapted as a thermistor, and a cable 36 for an electromagnetic position sensor 34. Passing through a second lumen 31 is a fluid irrigation tubing 38 to supply fluid to the electrode assembly 19. For at least uni-directional deflection, a first puller wire 44a passes through a third, off-axis lumen 32. For bi-directional deflection, a second puller wire 44b passes through a fourth, off-axis lumen 33.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the positions of the lumens 32, 33 for the puller wires 44a, 44b. The lumens 32, 33 should be off-axis, and diametrically opposite of each other for bi-directional deflection along a plane.

The useful length of the catheter, i.e., that portion that can be inserted into the body can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIGS. 4A and 4B. The proximal end of the intermediate section 14 comprises an inner circumferential notch that receives the outer surface of the distal end of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

With reference to FIGS. 5 and 5A, distal the intermediate section 14 is the distal electrode assembly 19 which includes an elongated, generally cylindrical, dome electrode 50 has a thin shell 57 and a plug 58. The shell 57 has an enlarged distal portion 51 with an atraumatic dome-shaped distal end 52. The distal portion defines a cavity or fluid chamber 53 that is in communication with an opening 54 at proximal end 55. Both the distal portion 52 and the proximal portion 55 have a circular cross-section although the diameter of the proximal portion may be slightly lesser than the diameter of the distal portion, and thus, there may be a transitional section 56 in between, forming a "neck". The shell 57 provides irrigation apertures 60 through which fluid entering and filling the chamber 53 can exit to outside of the dome electrode 50. In one embodiment, there are 56 irrigation apertures in total, with a greater portion of the apertures formed in radial wall 62, arranged in offset rows, and a lesser portion of the apertures formed in distal wall 64.

The plug 58 is shaped and sized to fit in and provide a fluid-tight seal of the opening 54 of the shell 57. In the illustrated embodiment, the plug is disc-shaped. Formed in the proximal face of the plug is a blind hole 72 receiving a lead wire 40D for the dome electrode 50. The plug also has a plurality of through-holes to allow passage of components and the like into the fluid chamber 53. In the illustrated embodiment, the plug has four through-holes 74, 75, 76, 77. Passing through each of through-holes 74, 75, 76 is a pair of thermistor wires 41/42. Received in through-hole 77 is the distal end of the irrigation tubing 38 allowing fluid delivered through the tubing 38 to enter the chamber 53. The plug and shell may be made of any suitable electrically-conductive material, such as palladium, platinum, iridium and combinations and alloys thereof, including, Pd/Pt (e.g., 80% Palladium/20% Platinum) and Pt/Ir (e.g., 90% Platinum/10% Irridium).

Advantageously, the wires 41/42 are sealed, insulated and protected by a routing guide tube 80 that extends from a proximal face 59 of the plug 58 to a short distance distal or beyond an outer surface of the distal wall 64 of the dome electrode 50. The guide tube is also used to electrically isolate the routed members from the surrounding dome electrode. The guide tube may be made of any suitable material that is fluid-tight, electrically-nonconductive, thermally-insulating, and sufficiently flexible, e.g., polyimide, to form a thin-walled tubing. Accordingly, the wires are protected from corrosive exposure to the fluid entering the chamber 53 and electrically-insulated from the shell 57. The guide tube offers many advantages including (i) routing components through the hollow dome electrode having a complex curvature, (ii) protecting the components through the hollow dome electrode, and (iii) insulating the components to minimize cooling effects of fluid flowing through chamber.

The portion of the wires 41/42 extending through the guide tube 80 is potted along the length of the guide tube by a suitable material 84, e.g., polyurethane or epoxy, which is shaped to form an atraumatic distal end 86. The material should be corrosive fluid resistant, and be able to provide structural support and prevent large thermal gradients within the guide tubes that may otherwise result from exposure to irrigation fluid in the chamber 53. No air exists in the guide tube. It is understood that a suitable micro-thermistor may also be constructed using a pre-existing thermistor. As illustrated in FIG. 19, a pre-existing thermistor (including wires 41/42 previously encased in potting material 85) is inserted in guide tube 80 and sealed at the proximal portion with material 84. The guide tubes electrically isolate the routed member from the surrounding dome electrode.

As shown in FIG. 3, the distal end 86 and most, if not all, of the exposed distal portion of the micro-element 20 come in direct contact with the tissue 22 by forming a micro-depression 24 in the tissue and nesting therein so that at least the distal end if not also the exposed portion of the micro-element 20 is buried, enveloped, encapsulated and/or surrounded by tissue. Such direct contact with and probing of the tissue enables more accurate sensing.

The distal portion of each guide tube 80 extends through an aperture 88 formed in the shell 57 of the dome electrode 50. In the illustrated embodiment, the apertures 88 are generally aligned with the through-holes in the plug 58 and they are formed along the circumferential corner 90 of the dome electrode 50 generally between the radial wall 62 and the distal wall 64 so that the guide tube 80 extends at an angle a of about 45 degrees relative to a longitudinal axis 92 of the dome electrode. The guide tubes can be held in position by adhesive or can sit naturally if designed with a slight interference fit with the apertures 88. As such, there can be both a distal component and a radial component in the orientation of protrusion of the exposed distal portion of the micro-element 20. It is understood however that the location and/or angle $\alpha$ may vary as desired. In typical applications, the distal component is greater than the radial component for improved and direct contact with tissue.

In one embodiment, the exposed portion of the micro-elements extending outside of the shell has a length D ranging between about 0.2 mm and 1.0 mm, preferably between about 0.3 mm and 0.6 mm, and more preferably about 0.5 mm. Each micro-element may have a diameter ranging between about 0.01 inch to 0.03 inch, preferably about 0.0135 inch. Although the illustrated embodiment has three micro-elements, with their distal ends arranged equi-distance from each other in a radial pattern, at about 0 degrees, 120 degrees and 240 degrees about the longitudinal axis of the dome electrode (FIG. 6), it is understood that the plurality of micro-elements may vary, ranging between about two and six, and the angular position of the micro-elements may vary as well.

Figure 7C:
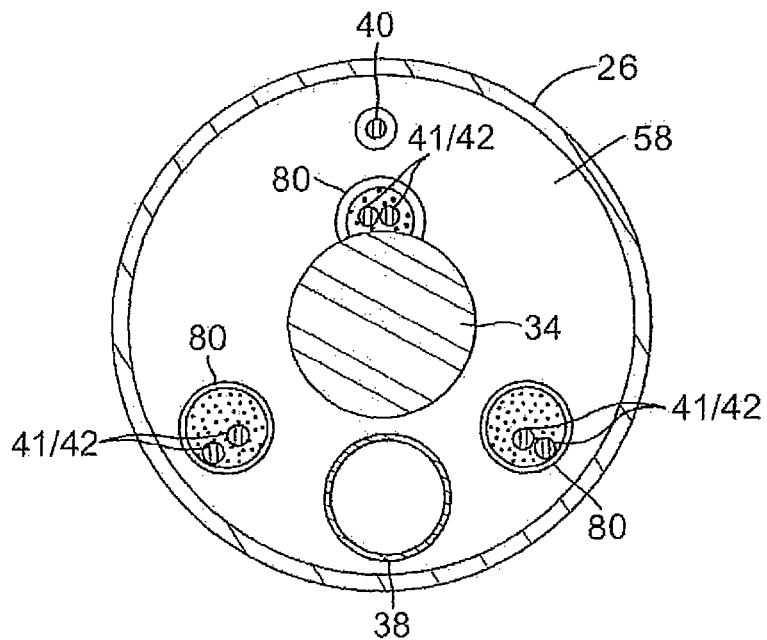
FIG. 7C is a distal end cross-sectional view of the portion of FIG. 7B, taken along line C-C.

With reference to FIGS. 7A, 7B and 7C, extending between the distal end of the intermediate section 14 and the dome electrode 50 is a connection portion 29 comprising a tubing 26. The tubing can be single-lumened and be made of any biocompatible plastic such as PEEK. The tubing provides space so that the components extending between the intermediate portion 14 and the dome electrode 50 to be reoriented as needed. Moreover, the position sensor 34 is housed within the tubing 26.

All of the wires pass through a common nonconductive protective sheath 45 (FIG. 4A), which can be made of any suitable material, e.g., polyimide, in surrounding relationship therewith. The sheath 45 extends from the control handle 16, through the catheter body 12 and to the intermediate section 14.

The pair of deflection puller wire 44a, 44b are provided for deflection of the intermediate shaft 14. The puller wires 44a, 44b extend through the central lumen 18 of the catheter body 12 and each through a respective one of the lumens 32 and 33 of the intermediate section 14. They are anchored at their proximal ends in the control handle 16, and at their distal end to a location at or near the distal end of the intermediate section 14 by means of T-bars 63 (FIG. 7B) that are affixed to the sidewall of the tubing 15 by suitable material 65, e.g., polyurethane, as generally described in U.S. Pat. No. 6,371,955, the entire disclosure of which is incorporated herein by reference. The puller wires are made of any suitable metal, such as stainless steel or Nitinol, and is preferably coated with Teflon® or the like. The coating imparts lubricity to the puller wire. For example, each puller wire has a diameter ranging from about 0.006 to about 0.010 inch.

As seen in FIG. 4B, each puller wire has a respective compression coil 64 in surrounding relation thereto. Each compression coil 67 extends from the proximal end of the catheter body 12 to at or near the proximal end of the intermediate section 14 to enable deflection. The compression coils are made of any suitable metal, preferably stainless steel, and are each tightly wound on itself to provide flexibility, i.e., bending, but to resist compression. The inner diameter of the compression coils is preferably slightly larger than the diameter of a puller wire. The Teflon® coating on the puller wire allows it to slide freely within the compression coil. Within the catheter body 12, the outer surface of the compression coil is covered by a flexible, non-conductive sheath 66, e.g., made of polyimide tubing. The compression coils are anchored at their proximal ends to the outer wall 30 of the catheter body 12 by proximal glue joints and to the intermediate section 14 by distal glue joints.

Within the lumens 32 and 33 of the intermediate section 14, the puller wires 44a, 44b extend through a plastic, preferably Teflon®, puller wire sheath 69 (FIG. 4B), which prevents the puller wires from cutting into the wall of the tubing 15 of the intermediate section 14 when the intermediate section 14 is deflected.

Longitudinal movement of the puller wires 44a, 44b relative to the catheter body 12 for bi-directional deflection is accomplished by appropriate manipulation of the control handle 16. A deflection knob 94 (FIG. 1) is provided on the handle which can be pivoted in a clockwise or counterclockwise direction for deflection in the same direction. Suitable control handles for manipulating more than one wire are described, for example, in U.S. Pat. Nos. 6,468,260, 6,500, 167, and 6,522,933 and U.S. application Ser. No. 12/960,286, filed Dec. 3, 2010, the entire disclosures of which are incorporated herein by reference.

The position sensor 48 can be a 3-coil electromagnetic sensor, or an assembly of single axis sensors ("SASs"). The position sensor enables the electrode assembly 19 (including the connection portion 29 housing the sensor) to be viewed under mapping systems manufactured and sold by Biosense Webster, Inc., including the CARTO, CARTO XP and NOGA mapping systems. Suitable SASs are described in U.S. application Ser. No. 12/982,765, filed Dec. 30, 2010, the entire disclosure of which is incorporated herein by reference.

With reference to FIGS. 8-13, an alternate embodiment of a catheter with a distal electrode assembly 19' is illustrated. Structural similarities exist between the embodiments disclosed herein. Accordingly, similar structures are identified by similar reference numerals.

Figure 8:
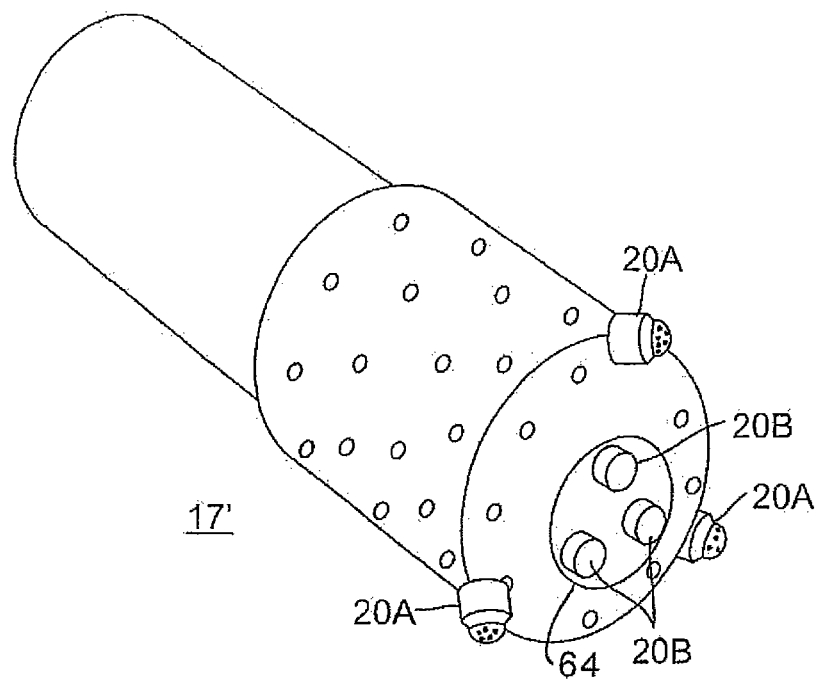
FIG. 8 is a perspective view of an electrode assembly in accordance with another embodiment of the present invention.
Figure 10:
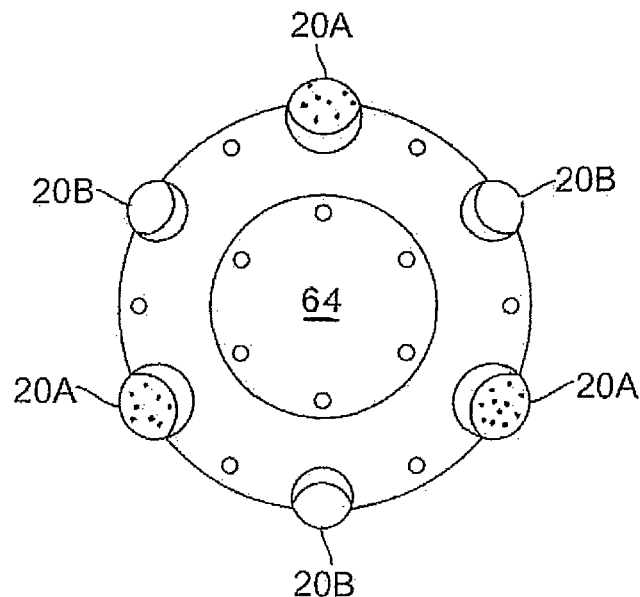
FIG. 10 is an end view of an electrode assembly in accordance with another alternate embodiment of the present invention.
Figure 12C:
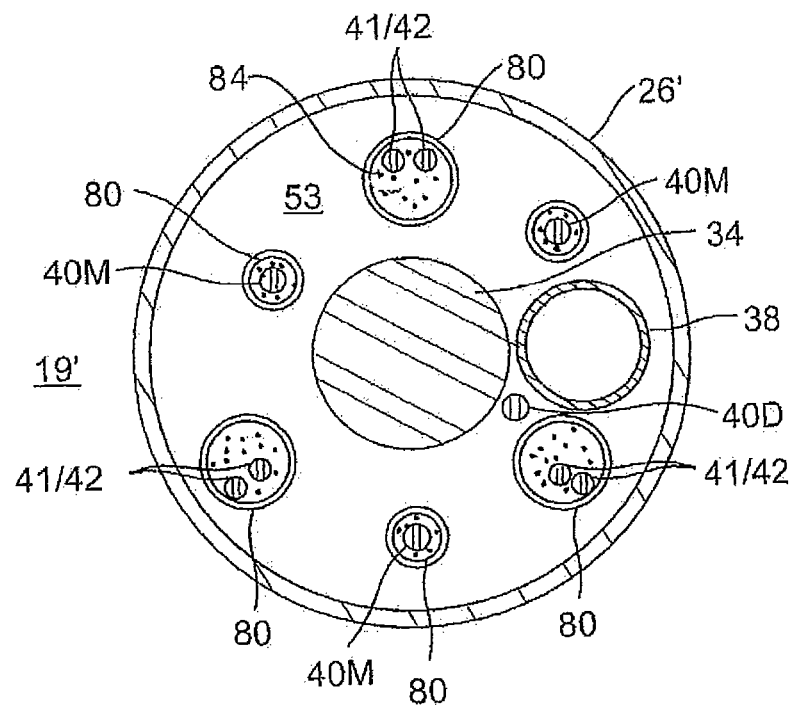
FIG. 12C is an end cross-sectional view of the connection portion of FIG. 12B, taken along line C-C.
Figure 13:
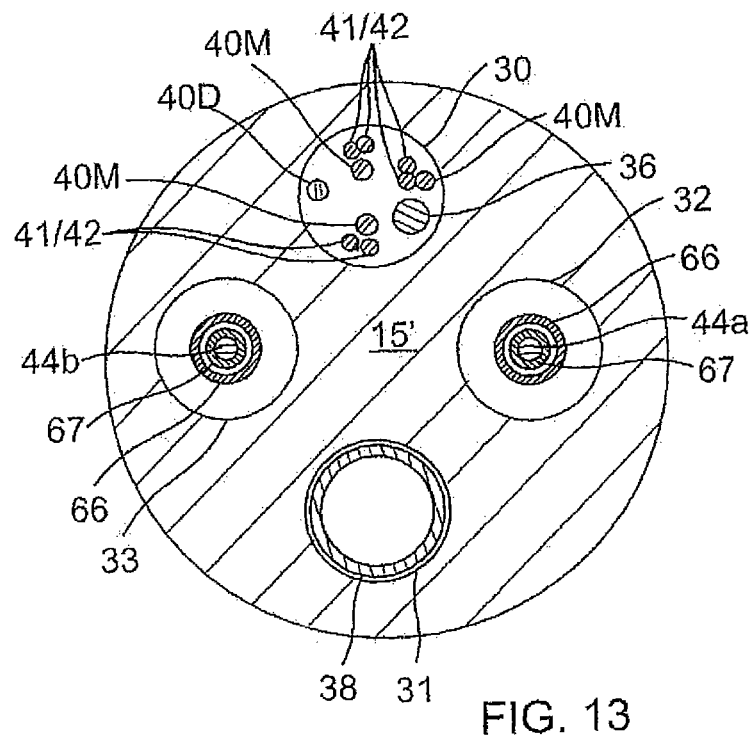
FIG. 13 is an end cross-sectional view of the intermediate deflectable section (near its proximal end) suitable for the electrode assembly of FIG. 8.

In the embodiment of FIGS. 8 and 9, a distal electrode assembly 19' has a first plurality of micro-elements 20A configured as thermistors, and a second plurality of micro-elements 20B configured as micro-electrodes, where each plurality may range between about two and six, and the first and second pluralities may be equal or unequal. In the illustrated embodiment, the first and second pluralities are equal, namely, three each, and the distal ends of micro-thermistor and the micro-electrodes can be interspersed along a common circumference on the distal wall (FIG. 10), or each occupy their own circumference on the distal wall (FIG. 11), with the micro-electrodes occupying an inner circumference and the micro-thermistors occupying an outer circumference. In either case, the distal ends of one group of micro-thermistors are arranged equi-distant from each other, in a radial pattern interspersed between each other, at about 0 degree, 120 degree and 240 degree about the longitudinal axis of the dome electrode, and the distal ends of the other group of micro-electrodes are arranged equi-distant from each other, in a radial pattern at about 60 degree, 180 degree and 300 degree.

Each micro-electrode has its respective guide tube 80 and lead wire 40M. In the illustrated embodiment, micro-electrode member 83 (FIG. 9) of the micro-electrode is a solid, elongated cylindrical member arranged in axial alignment with the dome electrode 50. The lead wire 40M is soldered at its distal end to the cylindrical member and extends through the lumen of the guide tube 80. The cylindrical member is exposed at a distal end 102 of guide tube 80 for direct with tissue. In one embodiment, the lead wire 40M is a copper wire. In one embodiment, the diameter of the micro-electrode 20B about 0.011 inch.

The distal ends 102 of the micro-electrodes 20B and the distal ends 86 of the micro-thermistors 20A come in direct contact with the tissue by forming micro-depressions in the tissue and nesting therein so that the distal ends are buried, enveloped, encapsulated and/or surrounded by tissue. Such direct and probing contact enables more accurate sensing by both the micro-electrodes and the micro-thermistors. However, as illustrated in the alternate embodiment of FIG. 2A, it is understood that the distal ends 102 and 86 may be flush with an outer surface of the shell of the dome electrode, so that the micro-electrodes 20A and 20B have no exposed portions or protrusions beyond the outer surface of the wall of the shell. The proximal ends of tubings 80 may also extend proximally of the proximal face of the plug 58, as desired or needed.

The plug 58' of the dome electrode 50 is configured with through-holes 106 for micro-electrode lead wires 40M with their guide tubes 80. Apertures 88 are provided in the shell 57' for these guide tubes 80. Again, position of the through-holes in the plug 58' is not critical. In the illustrated embodiment, the through-holes 106 are generally axially aligned with respective apertures 88 in the shell 57'.

With reference to FIGS. 12A, 12B, 12C and 13, proximal of the dome electrode 50' and the connection portion 29', the lead wires 40M (along with the thermistor wires 41/42, the position sensor cable 46 and the lead wire 40D for the dome electrode) extend through the first lumen 30 of the tubing 15 of the intermediate section 14, and through the central lumen 18 of the catheter body where they enter the control handle 16.

With reference to FIGS. 14-18, another alternate embodiment of a catheter with a distal electrode assembly 19" is illustrated. Structural similarities exist between the various embodiments disclosed herein. Accordingly, similar structures are identified by similar reference numerals.

Figure 14:
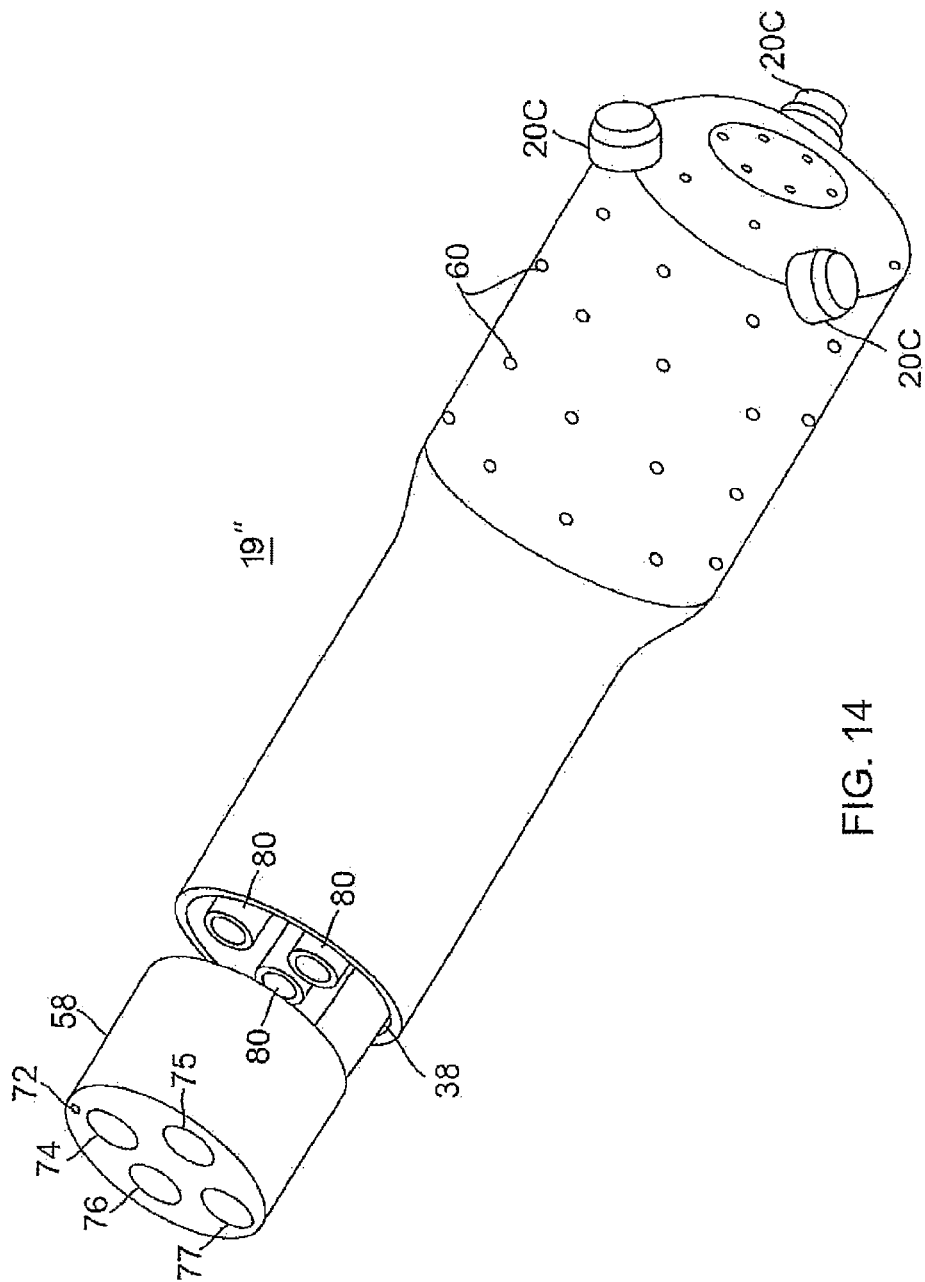
FIG. 14 is a partially exploded perspective view of an electrode assembly in accordance with yet another embodiment of the present invention.
Figure 15B:
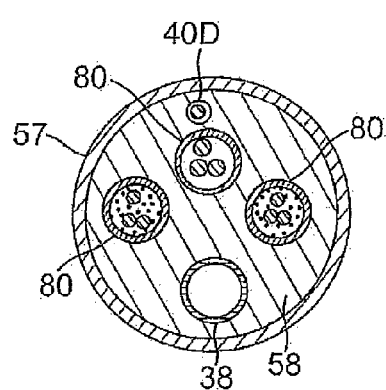
FIG. 15B is an end cross-sectional view of the electrode assembly of FIG. 15, taken along line B-B.
Figure 15C:
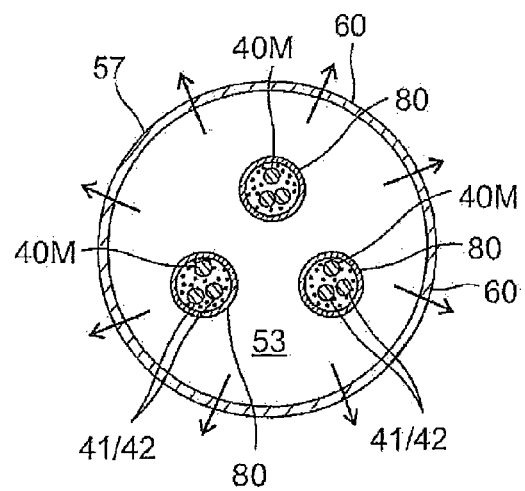
FIG. 15C is an end cross-sectional view of the electrode assembly of FIG. 15, taken along line C-C.
Figure 15D:
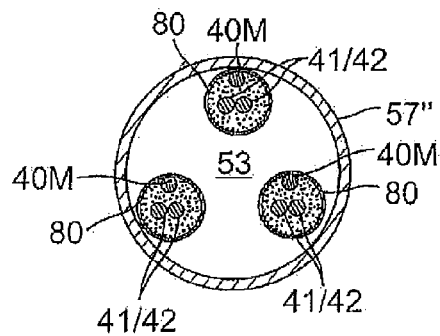
FIG. 15D is an end cross-sectional view of the electrode assembly of FIG. 15, taken along line D-D.
Figure 17A:
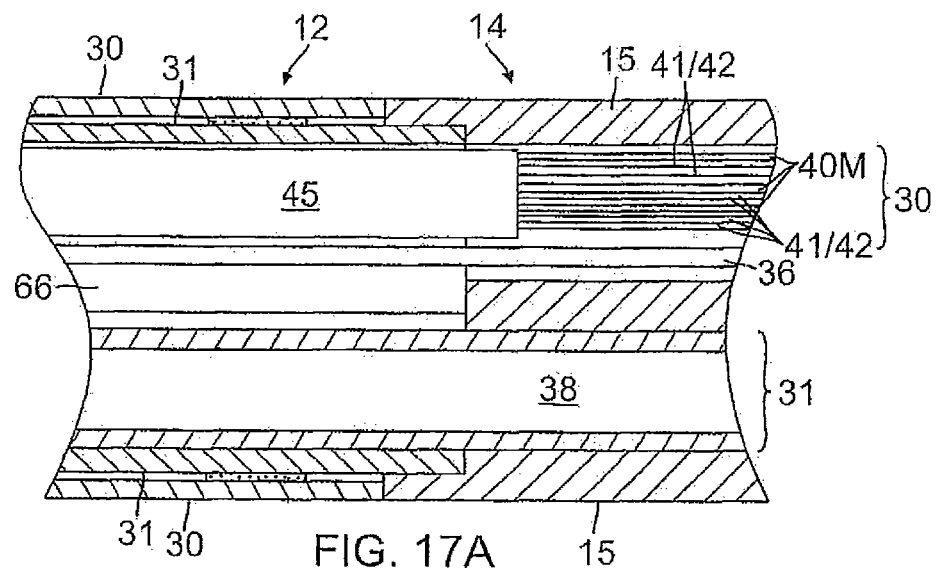
FIG. 17A is a side cross-sectional view of an embodiment of a junction between an intermediate deflectable section and a catheter body suitable for the electrode assembly of FIG. 15, taken along one diameter.
Figure 17B:
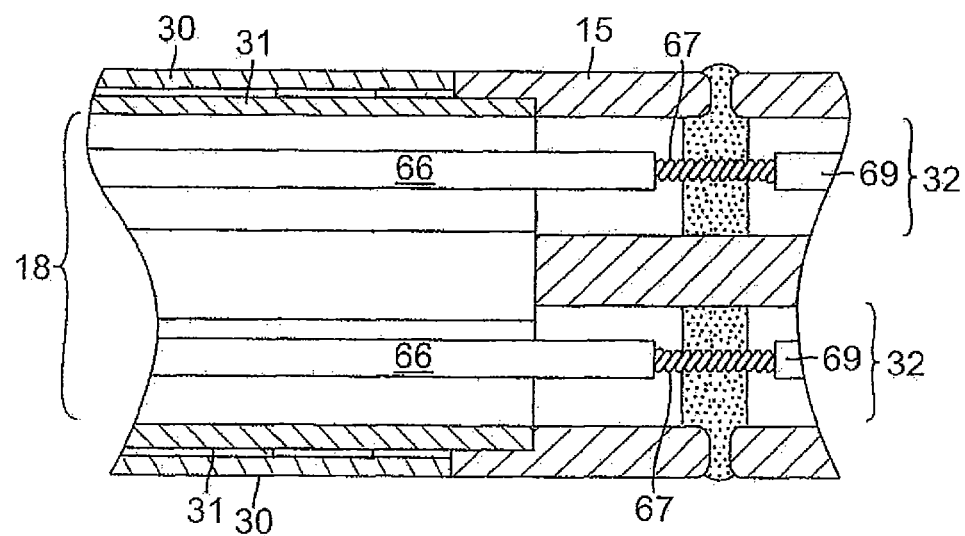
FIG. 17B is a side cross-sectional view of an embodiment of the junction between an intermediate deflectable section and a catheter body suitable for the electrode assembly of FIG. 15, taken along another diameter.

In the embodiment of FIGS. 14-16, the distal electrode assembly 19" has a plurality of micro-elements 20C, each configured to function both as a micro-thermistor and a micro-electrode within a single common guide tube. In the illustrated embodiment, the thermistor wires 41/42 extend through the guide tube 80 in a manner as previously described. The electrode member of the micro-element takes the form of a shell cap 110 is mounted on the distal ends of the thermistor wires 41/42. Best shown in FIG. 15A, the shell cap 110 is cup-shaped with a proximal cylindrical portion 112 defining an opening and a distal portion with a generally U-shaped cross-section. The shell cap can be made of any suitable electrically conductive material, for example, palladium, platinum, iridium and combinations and alloys thereof, including, Pd/Pt (e.g., 80% Palladium/20% Platinum) and Pt/Ir (e.g., 90% Platinum/10% Irridium). The shell cap can have a thickness ranging between about 0.005 inch and 0.001 inch, preferably about 0.002 inch. The length of the proximal portion can vary. The longer the length the more structural support is provided to the micro-element. The length can be about half the length of the shell. The opening of the shell cap sits inside the distal end of the guide tube such that an outer circumferential surface of the opening 112 of the cap interfaces an inner circumferential surface of the distal end of the guide tube 80. Soldered to a location on the outer or inner circumferential surface of the cap 110 is a distal end of the lead wire 40M which extends proximally through the lumen of the guide tube 80 along with the thermistor wires 41/42. The lead wire 40M and the thermistor wires 41/42 are isolated from each other by a suitable electrically nonconductive and non-thermally insulative material 84, e.g., polyurethane or epoxy, that fills the lumen of the guide tube 80. In the illustrated embodiment, there are three dual-function micro-electrodes 20C, with their distal ends arranged equi-distant from each other, in a radial pattern at about 0 degree, 120 degree and 240 degree about the longitudinal axis of the dome electrode. It is understood that the plurality and angular position may be varied as desired. The plurality may range between about two and six, preferably about three.

The distal end of each micro-element comes in direct contact with the tissue by forming a micro-depression in the tissue and nesting therein so that the distal end is buried, enveloped, encapsulated and/or surrounded by tissue. Such direct and probing contact enables more accurate electrical and thermal sensing.

The plug 58" is configured with through holes 74-76 for micro-elements 20C with their guide tubes 80, through-hole 77 for irrigation tubing 38, and blind-hole 72 for dome electrode lead wire 40D. Apertures 88 are provided in the shell 57" wall for the micro-elements 20C. Again, position of the through-holes is not critical. In the illustrated embodiment, the through holes 74-76 in the plug are generally axially aligned with respective apertures 88 in the shell.

With reference to FIG. 16A, 16B, 17A and 17B, proximal the dome electrode 50" and the connection portion 29", the lead wires 40M (along with the thermistor wires 41/42, the position sensor cable 46 and the lead wire 40D for the dome electrode) extend through the first lumen 30 of the tubing 15 of the intermediate section 14, and through the central lumen 18 of the catheter body where they enter the control handle 16.

FIGS. 18 and 18A illustrate an alternate embodiment of a dual-function micro-element 20D. Thermistor wires 41/42 are encased in a suitable sealant 84, e.g., polyurethane or epoxy. The sealed wires are then coated with a coating 120 of electrically conductive material, e.g., gold impregnated epoxy, which serves as the micro-electrode member. Lead wire 40M is connected to the coating 120. The sealed and coated wires are further encased in a guide tube 80 to electrically isolate the wires and the coating from the dome electrode. Where the distal ends of micro-element protrudes beyond the outer surface of the wall of the shell, the distal end of the sealed and coated wires are exposed radially and distally (FIG. 18). Where the distal ends of micro-elements are flush with the outer surface of the wall of the shell, the distal end of guide tubes 80 is coextensive with the distal end of the sealed and coated wires, leaving only the distal face exposed (FIG. 18B).

All of the through-holes in the plug in each embodiment is sealed around the guide tubes with any suitable sealant or adhesive, for example, polyurethane to prevent fluid leakage. The adhesive is first applied to the distal face of the plug prior to being pressed into the shell. After the electrode assembly is constructed, adhesive is applied to the proximal face of the plug for additional confidence in no fluid leakage. Components extending through the guide tubes, including lead wires and thermistor wires, can be anchored proximally in the catheter, for example, in the intermediate section 14, to provide strain relief.

It is also understood that the distal ends of the micro-elements may be flush with the radial and distal walls of the shell. That is, while the aforementioned embodiments provide micro-elements with a distal end that protrudes from the shell, the present invention includes a distal electrode assembly wherein the distal ends of the micro-elements are coextensive with the outer surface of the shell and do not protrude beyond it. After the electrode assembly is constructed, any protruding distal ends of the micro-elements can be buffed away until the distal ends are even with the outer surface of the shell.

For the foregoing embodiments, the wire 41 of the wire pair is a copper wire, e.g. a number "40" copper wire and the wire 42 is a constantan wire. The wires of each pair are electrically isolated from each other except at their distal ends where they are twisted together. Moreover, lead wires 40D and 40M, thermistor wires 41/42, puller wires 44a and 44b, cable sensor 36 and irrigation tubing 38 extend proximally through the central lumen 18 of the catheter body 12 before entering the control handle where they are anchored or passed through to appropriate connectors or couplers inside the control handle or proximal thereof.

FIGS. 20A, 20B, 20C and 20D are perspective views of another embodiment of the present invention having a different configuration of thin shell 57" and plug 58". FIG. 20A depicts thin shell 57" in an unswaged form prior to being formed over plug 58" off FIG. 20B. FIG. 20B depicts plug 58" alone. FIG. 20C and 20D depicts perspective views from the proximal and distal ends of the combination of thin shell 57" and plug 58" after the proximal end portion of thin shell 57" has been swaged over plug 58" FIG. 21 depicts an end view of the proximal end of the swaged thin shell 57" over plug 58". FIG. 22 depicts the cross-sectional view of the swaged thin shell 57" over plug 58" taken through line A-A in FIG. 21.

Referring to FIGS. 20A-D, 21 and 22, the thin shell 57" has an enlarged distal portion 51" with an atraumatic dome-shaped distal end 52". The distal portion 51" and dome-shaped distal end defines a cavity or fluid chamber 53" that is in communication with an opening 54" at proximal end 55". Both the distal portion 51" and the proximal portion 55" have a circular cross-section although the diameter of the proximal portion in this embodiment is slightly lesser than the diameter of the distal portion, and thus, there is a transitional section 56" in between, forming a "neck". The shell 57" includes a plurality of irrigation apertures 60" through which fluid entering and filling the chamber 53" can exit to outside of the dome electrode. In one embodiment, there are 56 irrigation apertures in total, with a greater portion of the apertures formed in the wall of thin shell 57", arranged in offset rows, and a lesser portion of the apertures formed in atraumatic dome-shaped distal end 52".

Formed in the proximal face of the plug 58" is hole 72" for receiving a lead wire 40D for the dome electrode 50. The plug also has a plurality of through-holes to allow passage of components and the like into the fluid chamber 53". In the illustrated embodiment, the plug has four through-holes 54", 75", 76", 77". Passing through each of through-holes 74", 75", 76" is a pair of thermistor wires 41/42 (shown in previous embodiments). Received in through-hole 54" is the distal end of the irrigation tubing 38 allowing fluid delivered through the tubing 38 to enter the chamber 53". The plug and shell made be made of any suitable electrically-conductive material, such as palladium, platinum, iridium and combinations and alloys thereof, including, Pd/Pt (e.g., 80% Palladium/20% Platinum) and Pt/Ir (e.g., 90% Platinum/10% Irridium). The shell is in this embodiment is preferably around 0.0035 inches. Plug 58" has a slightly large diameter at its proximal most end and a slightly smaller diameter where the shell 57" is swaged creating a smooth transition.

In manufacture, plug 58" is placed inside the proximal end of thin shell 57" and then thin shell 57" is crimped or swaged to fit around the distal end of plug 58". Proximal end of plug 58" has a slightly larger outer diameter approximately equal to the thickness of thin shell 57" after swaging. This assembly provides an integrated plug and shell as well as support in the transitional section 56" of the shell. After swaging, the assembly may now be used to hold the other micro-element components of a device in accordance with the present invention.

FIG. 23 is a cross-sectional view of another embodiment of the present invention having a plastic insert used to align the microelectrode assemblies in the thin shell 57. Plastic insert 98 has a distal end that rests inside the distal end of thin shell 57. FIG. 24 is a perspective view and FIG. 25 is an end view from the distal end of the plastic insert 98 of the embodiment shown in FIG. 23. Plastic insert 98 is comprised of a biocompatible material preferably a thermoplastic or thermoset material such as polycarbonate or polyurethane. Preferably, the material is selected to provide thermal insulation from the surrounding irrigation fluid, i.e., saline, flow. Plug insert 98 has three frusto-conical cut-out sections 99a, 99b and 99c each separated from another by approximately 120 degrees. These cut-out sections are designed to each receive one of three micro-elements, i.e., microelectrode and/or microthermistor assemblies, with a fourth assembly going through axially aligned hole 99d. Plastic insert 98 and the microelements may be injection molded to form one assembly for ease of manufacturing the catheter. There are three guiding pins 101a, 101b and 101c that are placed 120 degrees apart in order to facilitate placement of the plastic insert into the dome electrode. The guiding pins are designed to mate with three holes in the dome electrode 50 in order to align the frusto-conical cut-out sections 99a, 99b and 99c with the opening in the dome electrode. The arrangement of the guiding pins as well as the configuration of the frusto-conical cutouts may vary without departing from the spirit of the invention.

FIGS. 26-29 depict an addition to the catheter of the present invention which adds a pressure or force-sensing capability to the catheter having micro-elements described hereinabove. The pressure indication may be used by the operator of catheter 10' to ensure that the distal tip is pressing against the endocardium firmly enough to give the desired therapeutic or diagnostic result, but not so hard as to cause undesired tissue damage. U.S. Patent Application 20090093806, to Govari et al., filed Oct. 8, 2007, whose disclosure is incorporated herein by reference, describes a system that uses a pressure-sensing catheter in this manner. Catheter 10' may be used in such a system.

Figure 26:
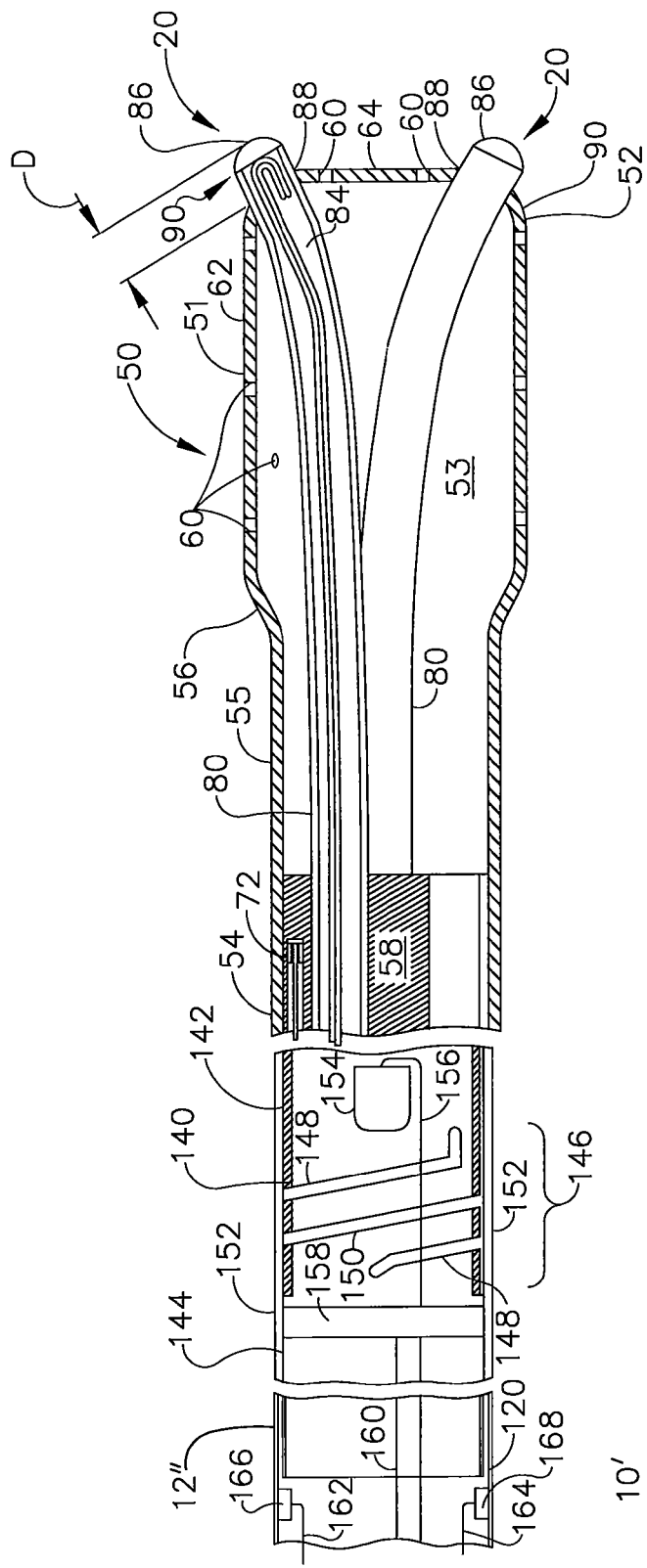
FIG. 26 is a schematic sectional view of the pressure sensor embodiment of the present invention.

FIG. 26 is a schematic, sectional view of catheter 10', showing details of the distal end of the catheter, according to an embodiment of the present invention. A coupling member 140 forms joint between distal tip 124 and the distal end of elongated catheter body 12' and is disposed between dome electrode 50 and the distal end of the elongated catheter body 12'. By way of example, coupling member 140 is assumed to be formed in two parts, a first part 142 and a second part 144, the two parts being fixedly joined together. The two parts of coupling member 140 are generally tubular, and are joined so that the coupling member also has a tubular form. Although there is no necessity that coupling member 140 be formed of two parts, the two part implementation simplifies assembly of a magnetic field generator and magnetic position sensor into the member, as is described in more detail below. The two part implementation is typically also facilitated by incorporating an attaching stem into one of the parts, as is also described in more detail below.

Coupling member 140 has a plurality 146 of intertwined helices cut along a portion of the length of first part 142 of the member. Plurality 146 may comprise any integral number of single helices greater than one, such as, but not limited to two, three or four helices. For simplicity, unless otherwise stated, in the following description the plurality is assumed to comprise two intertwined single cut helices, a first cut helix 148 and a second cut helix 150, and is also referred to herein as a double helix. Those having ordinary skill in the art will be able to adapt the description without undue experimentation, to encompass a plurality of intertwined helices where the plurality is more than two single helices.

Coupling member 140 (along with the distal end of catheter 10' generally) is typically covered by a flexible plastic sheath 152. When catheter 10' is used, for example, in ablating endocardial tissue by delivering RF (radio-frequency) electrical energy through irrigated electrode dome 50 (which may also be any of the other configurations disclosed herein), considerable heat is generated in the area of distal tip. For this reason, it is desirable that sheath 152 comprises a heat-resistant plastic material, such as polyurethane, whose shape and elasticity are not substantially affected by exposure to the heat.

Catheter 10' comprises a position sensor 154 within a distal portion of first part 142. The position sensor is connected via a conductor 156 to a processing unit 232 (shown in FIG. 30 and described below) at the proximal end of elongated catheter body 12'. Conductor 156 may typically comprise a twisted-pair cable. Position sensor 154 is configured to sense the position of the distal tip having the electrode dome 50 relative to the distal end of elongated catheter body 12'. As explained above, the position changes in response to deformation of the coupling member, and the processing unit may thus use the position reading in order to give an indication of the pressure exerted on and by the distal tip.

Position sensor 154 may comprise one or more coils, which are configured to generate signals in response to a magnetic field. These signals are indicative of the position and orientation of distal tip 124. The magnetic field may be produced by a miniature magnetic field generator 158 located within second part 144 of the coupling member. Generator 158 is typically activated by the proximal end processing unit 232, via a conductor 160. Thus, when coupling member 140 bends, the signals generated by the position sensor change and can be analyzed by the processing unit to determine the pressure on the distal tip. Additional magnetic fields may be generated by field generators (not shown) in fixed locations external to the patient's body. These fields cause position sensor 154 to generate additional signals that are indicative of the position and orientation of distal tip dome electrode 50 in the fixed frame of reference of the external field generators. These aspects of the operation of position sensor 154 are described in detail in the above-mentioned U.S. patent application Ser. No. 11/868,733. They are outside the scope of the present invention.

Catheter 10' may also comprise a pair of pull-wires 162, 164 for use by an operator in steering the catheter. The pull-wires pass through elongated catheter body 12' and are anchored at respective anchor points 166, 168 in the distal end of the elongated catheter body, typically on opposite sides of the tube. The operator tightens the pull-wires (typically by turning a knob—not shown—at the proximal end of the catheter) in order to bend the distal end of the catheter either "up," or "down." (The references to "up" and "down" are purely with respect to FIG. 2, and are not to be construed as limiting the motion of the catheter in any particular direction.) When the operator releases the pull-wires, the catheter straightens due to the resilience of the elongated catheter body.

Figure 27:
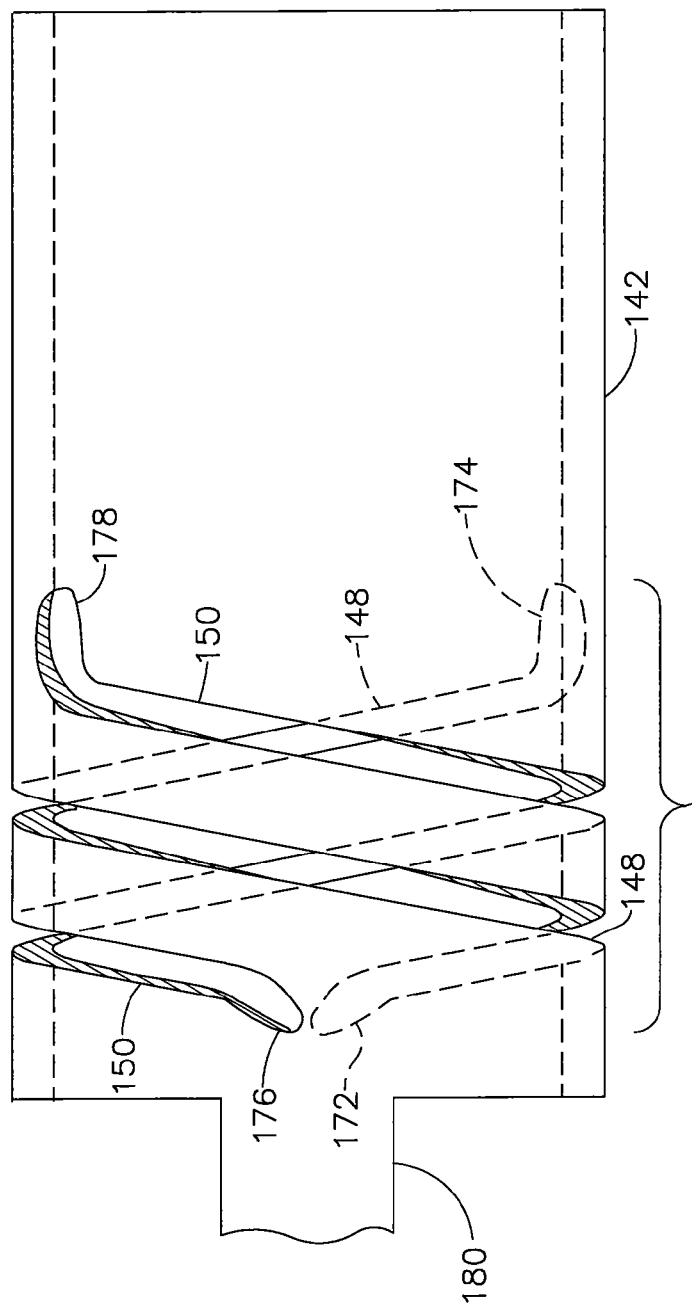
FIG. 27 is a schematic side view of a portion of a coupling member, according to an embodiment of the present invention.

FIG. 27 is a schematic side view of first part 142 of coupling member 140, according to an embodiment of the present invention. FIG. 28 is a schematic perspective view of the two parts joined to form the coupling member, and FIG. 29 is a schematic section of the coupling member, according to embodiments of the present invention.

Both parts of coupling member 140 comprise generally tubular pieces of an elastic material, typically a metal material. The elastic material is typically the same for both parts, for example, a superelastic alloy such as nickel titanium (Nitinol). For intracardiac applications, the overall length of member 140 may be approximately 8.5 mm, with an outer diameter of approximately 2.0 mm. Second part 144 is in the form of a cylinder having a length of approximately 5.2 mm and a wall thickness of approximately 0.08 mm. First part 142 has a wall thickness of approximately 0.27 mm. Alternatively, in other applications, the parts of coupling member 40 and its overall dimensions may be larger or smaller.

As shown in FIG. 27 and as stated above, first part 142 of coupling member 140 has two intertwined single helices cut into the part, first helix 148 and second helix 150. The two helices may be cut by laser machining of the first part. For the dimensions given above, each helix is typically opened by the laser to a width of about 0.1 mm. While the widths of each helical cut are typically the same, there is no requirement that this is the case, and some embodiments may have the helical cuts of different widths. Furthermore, in some embodiments the width of one or both of the cuts may be varied along the cut, typically to add strength to member 140.

To give an appropriate balance between flexibility and stiffness for intracardiac applications, each helix typically subtends an angle between approximately 360° and approximately 720° about a central axis 170 (FIG. 28) of member 140. For the intracardiac applications described above, and as illustrated in FIG. 27, each helix subtends about 450°, so that each helix has an angular extent of approximately 1.25 turns. Alternatively, larger or smaller angular extents may be used for each helix, and the angular extents may not be equal, depending on application requirements.

The terminations of each helix of part 142 may be enlarged for the purposes of strain relief so that the part does not break during use. The enlargement is typically in the form of a partial ellipse. Thus, helix 148 terminates in a first partial ellipse 172 and a second partial ellipse 174, and helix 150 terminates in a first partial ellipse 176 and a second partial ellipse 178. In some embodiments the enlargements may be implemented as portions of circles having a diameter greater than the width of the helix. The enlargements may be oriented in relation to their respective helices so as to minimize the length of part 142, and so that, consequently, the distance between position sensor 154 and generator 158 may be minimized.

The helices of plurality 146 have rotational symmetry about axis 170, according to the number of helices in the plurality. Thus, the double helix described herein has 2-fold rotational symmetry. In general, if plurality 146 comprises n helices, where n is a positive integer, the helices are configured to have n-fold rotational symmetry about axis 170.

The configuration of the multiple helices of plurality 146 may be compared to the configuration of threads of a multiply-threaded screw, also termed a multiple-start screw. (In the same way, a single helix may be compared to the thread of a single-threaded, or single-start, screw.) Using this comparison, for the embodiment exemplified above (wherein the overall length of member 40 is approximately 8.5 mm), plurality 146 corresponds to a doubly-threaded screw having a pitch of approximately 0.5 mm, and a lead that is double this value, i.e., approximately 1.0 mm.

First part 142 typically comprises a generally rectangular stem 180, to be used in attaching part 142 to second part 144. The stem may be formed by cutting material from the tube used to produce part 142, so that the stem has the same wall thickness as the wall thickness of the remainder of part 142.

As illustrated in FIG. 28, member 140 is formed by sliding first part 142 into second part 144, so that stem 180 is enclosed by part 144, and so that partial ellipses 172 and 176 approximately contact the edge of part 144. Once positioned as shown to have a common circumference, the two parts are then fixedly connected together, typically by keyhole welding the edges of stem 180 to the inner surface of part 144. In addition, for extra rigidity, and as shown in FIG. 29, the two parts are also welded together where the edge of part 144 contacts part 142, i.e., around the common circumference. The circumferential welding is partial, so that regions 182, encompassing the helical cut terminations comprising partial ellipses 176 and 172, are not welded. The partial welding distributes the stresses between the two parts of the coupling member more symmetrically than that of a single helix, as well as reducing the stress at any one location by virtue of the two parts.

The plurality of helical cuts in coupling member 140 cause the member to behave as a spring, allowing the member to bend. By having more than one helical cut, the bending is more uniform than the bending (for the same range of external forces) as that of a tube with a single helical cut and the same number of turns as the plurality of cuts. The plurality of helical cuts also provides greater side stiffness compared to a tube with a single helical cut. The bending extends up to an angle, for example, 30°, at which the sides of the helical cuts on the inside of the bend come into contact. At this point, the locations in contact essentially become "inactivated," although the locations not in contact remain available for bending. The width of the helical cuts may thus be chosen to provide a desired, predetermined, angular limit on the initial bending of the coupling member, which is useful in preventing damage to components of catheter 10' that may be caused by excessive bending.

Furthermore, having a plurality of helical cuts eliminates the single point of failure that occurs with a single helical cut coupling member. Plurality 146 of helical cuts requires a corresponding plurality of failures for first part 142 of coupling member 140 to break.

Although the operation and construction of catheter 10' described above in the context of catheter-based intracardiac procedures, the principles of the present invention may similarly be applied in other therapeutic and diagnostic applications that use invasive probes, both in the heart and in other organs of the body.

Figure 30:
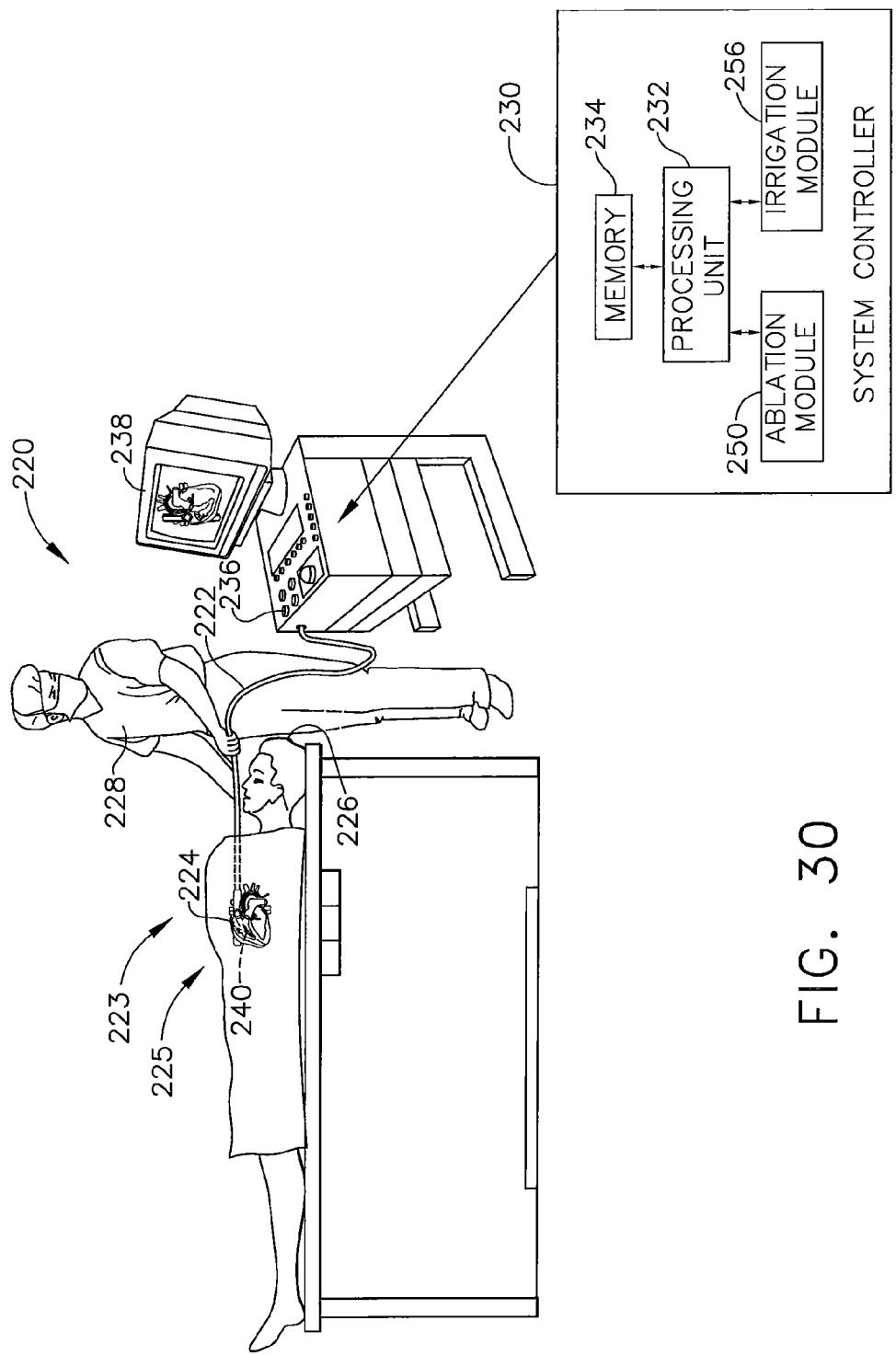
FIG. 30 is a schematic diagram of an ablation system incorporating the catheter of the present invention.

Reference is now made to FIG. 30 which describes a system for use with the catheter described hereinabove. An ablation system 220 uses an ablation catheter such as that described as catheter 10 or 10' above to effect ablation of tissue in a patient. In system 220, catheter 10 or 10' is inserted into a lumen 223, such as a chamber of a heart 224, of a subject 226. The catheter is used by operator 228 of system 220 during a procedure which includes performing ablation of body tissue 225.

The functioning of system 220 is managed by a system controller 230, comprising a processing unit 232 communicating with a memory 234, wherein is stored software for operation of system 220. Controller 230 is typically an industry standard personal computer comprising a general purpose computer processing unit. However, in some embodiments, at least some of the functions of the controller are performed using custom designed application specific integrated circuits (ASCIs) or a field programmable gate array (FPGA). Controller 230 is typically operated by the operator 228 using a pointing device 236 and a graphic user interface (GUI) 238 which enable the operator to set parameters of the system 220. GUI 238 typically also displays results of the procedure to the operator.

The software in memory 234 may be downloaded to the controller in electronic form, over a network, for example. Alternatively or additionally, the software may be provided on non-transitory tangible media such as optical, magnetic or electronic storage media.

System 220 is connected through cable 222 to the catheter 10 or 10'. Signals from the position sensor 154 are sent through conductor 156 which is operably connected to cable 22 and system 220 in order to provide a signal indicative of position of the position sensor which is then processed to provide an indication of the pressure on the dome electrode 50. Additionally, leads 40M from the microelectrodes, 41/42 from the microthermistors and 40D from the dome electrode are also connected to the system 220. Signals arriving on leads 40M to the microelectrodes are used by system 220 to provide impedance and ECG readings at the location of tissue touched by the microelectrode. Signals arriving on leads 41/42 from the microthermistors are used to provide a temperature reading at the location of the microthermistor. Lead 40D is used to send RF energy from the system 220 to cause the dome electrode to effect an ablation of tissue at the location targeted by the operator 228.

Typically, during an ablation, heat is generated by the RF energy in the tissue of the patient to effect the ablation and some of this heat is reflected to the dome electrode 50 causing coagulation at and around the electrode. System 220 irrigates this region through irrigation apertures 60 and the rate of flow of irrigation is controlled by the irrigation module 258 and the power (RF energy) sent to the dome electrode 50 is controlled by the ablation module 250. A saline temperature sensor (not shown) is located in the fluid irrigation tubing and provides a signal to measure a temperature of the irrigation fluid as one of the inputs to system controller 230.

The system controller uses input of the saline temperature, the impedance measurements from the microelectrodes, the sensed pressure reading and the input of the temperature at the microthermistors to determine the lesion size and depth. Part of this can be accomplished in accordance with U.S. patent application Ser. No. 13/113,159 entitled "Monitoring Tissue Temperature Using an Irrigated Catheter" the teachings of which are hereby incorporated by reference.

The microelectrodes may also provide intracardiac electrocardiograms to the system controller 230. ECG information may be used by the system controller to determine when the tissue site being ablated is no longer conducting the arrhythmogenic currents.

In operation, an operator 228, such as a cardiologist, inserts a guiding sheath through the vascular system of the patient so that the distal end of the guiding sheath enters a chamber of the patient's heart, for example, the left atrium. Operator then advances the catheter through the guiding sheath. The catheter is fed through the guiding sheath until at least the electrode assembly is past the distal end of the guiding sheath.

The operator can advance and retract the catheter in the left atrium and deflect the intermediate portion 14 as appropriate to aim the electrode assembly toward target tissue. The catheter is advanced until the distal end of the dome electrode contacts tissue. RF energy can be applied to the dome electrode to ablate the tissue for forming a lesion. Irrigation fluid is delivered via the irrigation tubing to the dome electrode where it enters the chamber and exits via the irrigation apertures for various purposes, including cool the dome electrode and keeping the surface free of char and coagulum. Additional normal force can be applied to so that the micro-elements depress the tissue and become nested in the tissue for direct contact which allows for more accurate sensing, including more accurate impedance measurement and more accurate temperature sensing. In the latter instance, deeper temperature sensing via the micro-elements provides a more accurate temperature reading of the tissue to avoid adverse effects of tissue overheating such as charring and steam pop, as opposed to merely the tissue surface temperature which can be biased by the cooling temperature of the irrigation fluid. Deeper impedance measurements are provides for more accurate measurements for various purposes including a determination of lesion size. Furthermore, impedance readings from the plurality of microelectrodes, temperature readings from the micro-thermistors and pressure (force) readings (magnitude and direction) from the tip of the catheter will enable the system to estimate the amount of tissue surrounded by the catheter enabling a better estimation of lesion depth and size.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
    an elongated body;
    a distal electrode assembly mounted on the elongated body comprising
        an electrode having a shell configured with an inner chamber, the shell having a wall defining a proximal portion and a distal portion, the wall of the distal portion having at least one aperture;
        a micro-element extending through the inner chamber between the proximal portion and the distal portion, the micro-element having a distal end received in the at least one aperture, the distal end being at least coextensive with an outer surface of the wall;
    and a pressure-sensing assembly comprising:
    a coupling member, which couples the distal electrode assembly to the distal end of the elongate body;
    a position sensor configured to sense a position of the distal tip relative to the distal end of the elongated body, the position changing in response to deformation of the coupling member;

a magnetic field generator within the distal end of the coupling member;
wherein the position sensor is configured to generate a signal in response to a magnetic field, and wherein the signal is indicative of a position of the distal tip.

2. The catheter of claim 1 wherein the coupling member comprises a tubular piece of an elastic material having a plurality of intertwined helical cuts therethrough along a portion of a length of the piece.

3. The catheter of claim 2 wherein at least one of the helical cuts comprises an enlarged termination.

4. The catheter of claim 3 wherein the enlarged termination comprises a partial ellipse.

5. The catheter of claim 2 wherein the plurality of intertwined helical cuts comprises n cuts, where n is an integer greater than 1, and wherein the cuts are configured so that the tubular piece has n-fold rotational symmetry about an axis of the piece.

6. The catheter of claim 2 wherein at least one of the helical cuts subtends an angle between 360° and 720° about an axis of the tubular piece.

7. The catheter of claim 2 wherein the coupling member is configured to bend in response to pressure exerted on the distal tip when the distal tip engages the tissue, and wherein at least one of the helical cuts has a width chosen so as to provide a predetermined angular limit on initial bending of the coupling member.

8. The catheter of claim 1, wherein the chamber is adapted to receive fluid and the chamber has a plurality of irrigation apertures configured to allow fluid to flow from inside the chamber to outside the chamber.

9. The catheter of claim 1, wherein the distal end of the micro-element includes an exposed portion outside of the wall of the shell.

10. The catheter of claim 1, wherein the micro-element includes a micro-electrode element at its distal end and the at least one wire is attached to the micro-electrode element.

11. The catheter of claim 1, wherein the micro-element has at least two wires adapted for temperature sensing.

12. The catheter of claim 1, further comprising a plurality of micro-elements each having a distal end, wherein the distal ends of the micro-elements are arranged in a radial pattern in the distal portion of the electrode about a longitudinal axis of the electrode.

13. The catheter of claim 12, wherein the plurality ranges between about two and six.

14. The catheter of claim 12, wherein the plurality is three.

15. The catheter of claim 12, wherein the plurality is six.

16. The catheter of claim 1, further comprising a first plurality of first micro-elements configured for impedance sensing and a second plurality of second micro-elements configured for temperature sensing,
wherein each of the first micro-elements has a tube housing a micro-electrode and a lead wire; and
wherein each of the second micro-elements has a tube housing a pair of wires configured for temperature sensing.

17. The catheter of claim 16, wherein distal ends of the first micro-elements are arranged in a radial pattern along a circumference of the distal portion of the shell about a longitudinal axis of the electrode.

18. The catheter of claim 16, wherein distal ends of the second micro-elements are also arranged in a radial pattern along the circumference, interspersed between the first micro-elements.

19. The catheter of claim 16, wherein the distal ends of the second micro-elements are arranged in a radial pattern along a different circumference of the distal portion of the shell about the longitudinal axis of the electrode.

20. The catheter of claim 9, wherein the exposed portion extends at an angle having a distal component and a radial component relative to the longitudinal axis of the electrode.

21. The catheter of claim 9, wherein the exposed portion has a length ranging between about 0.2 mm and 1.0 mm.

22. The catheter of claim 9, wherein the exposed portion has an atraumatic configuration adapted to form a micro-depression in tissue without breaching the tissue.

23. The catheter of claim 1, wherein the micro-element includes:
a guide tube with a lumen;
a pair of temperature-sensing wires having a electrically-conductive coating applied to a distal portion of the temperature-sensing wires; and
a lead wire attached to the coating,
wherein the temperature-sensing wires and lead wire extend through the lumen.

24. A catheter, comprising:
an elongated body;
a distal electrode assembly, including
an electrode having a shell configured with an inner chamber, the shell having a wall defining a proximal portion and a distal portion, the wall of the distal portion having a plurality of apertures;
a common plurality of micro-elements extending through the inner chamber between the proximal portion and the distal portion, each micro-element having a distal end received in a respective aperture, the distal end having an exposed portion outside of the shell; and
wherein the electrode is further comprised of a thin shelled swaged over a plug, the plug having holes for passage of the micro-elements into the inner chamber.

25. A catheter, comprising:
an elongated body;
a distal electrode assembly, including
an electrode having a shell configured with an inner chamber, the shell having a wall defining a proximal portion and a distal portion, the wall of the distal portion having a plurality of apertures;
a common plurality of micro-elements extending through the inner chamber between the proximal portion and the distal portion, each micro-element having a distal end received in a respective aperture, the distal end having an exposed portion outside of the shell; and
wherein the electrode comprises a plastic insert for holding a plurality of micro-elements at pre-determined radial spacings and guiding them through the apertures in the wall of the shell of the electrode.

26. The catheter of claim 25, wherein the plastic insert has a plurality of guiding pins to align the plastic insert and the apertures in the wall of the shell of the electrode.

27. A system for the ablation of the tissue of a patient comprising:
a catheter, comprising:
an elongated body;
a distal electrode assembly mounted on the elongated body comprising
an electrode having a shell configured with an inner chamber, the shell having a wall defining a proximal portion and a distal portion, the wall of the distal portion having at least one aperture;
a micro-element extending through the inner chamber between the proximal portion and the distal portion, the micro-element having a distal end received in the at least one aperture, the distal end being at least coextensive with an outer surface of the wall;

and a pressure-sensing assembly comprising:

a coupling member, which couples the distal electrode assembly to the distal end of the elongate body;

a position sensor configured to sense a position of the distal tip relative to the distal end of the elongated body, the position changing in response to deformation of the coupling member;

a magnetic field generator within the distal end of the coupling member;

wherein the position sensor is configured to generate a signal in response to a magnetic field, and wherein the signal is indicative of a position of the distal tip; and, a system controller capable of receiving signals from the position senor and the micro-elements and controlling the power to the distal electrode in order to control the size and depth of the ablation lesion created based on one of more of the following parameters: impedance, temperatures, ECG readings and pressure of the distal electrode against the tissue.

28. The system of claim 27, wherein the chamber is adapted to receive fluid and the chamber has a plurality of irrigation apertures configured to allow fluid to flow from inside the chamber to outside the chamber.

29. The system of claim 27, wherein the distal end of the micro-element includes an exposed portion outside of the wall of the shell.

30. The system of claim 27, wherein the micro-element includes a micro-electrode element at its distal end and the at least one wire is attached to the micro-electrode element.

31. The system of claim 27, wherein the micro-element has at least two wires adapted for temperature sensing.

32. The system of claim 27, further comprising a plurality of micro-elements each having a distal end, wherein the distal ends of the micro-elements are arranged in a radial pattern in the distal portion of the electrode about a longitudinal axis of the electrode.

33. A method for the ablation of a portion of tissue of a patient by an operator comprising:

inserting a catheter into the patient, wherein the catheter comprises:

an elongated body;

a distal electrode assembly mounted on the elongated body comprising an electrode having a shell configured with an inner chamber, the shell having a wall defining a proximal portion and a distal portion, the wall of the distal portion having at least one aperture;

a micro-element extending through the inner chamber between the proximal portion and the distal portion, the micro-element having a distal end received in the at least one aperture, the distal end being at least coextensive with an outer surface of the wall;

and a pressure-sensing assembly comprising:

a coupling member, which couples the distal electrode assembly to the distal end of the elongate body;

a position sensor configured to sense a position of the distal tip relative to the distal end of the elongated body, the position changing in response to deformation of the coupling member;

a magnetic field generator within the distal end of the coupling member;

wherein the position sensor is configured to generate a signal in response to a magnetic field, and wherein the signal is indicative of a position of the distal tip; and, connecting the catheter to a system controller capable of receiving signals from the position senor and the micro-elements and controlling the power to the distal electrode in order to control the size and depth of the ablation lesion created based on one of more of the following parameters: impedance, temperatures, ECG readings and pressure of the distal electrode against the tissue.

34. The method of claim 33, wherein the chamber is adapted to receive fluid and the chamber has a plurality of irrigation apertures configured to allow fluid to flow from inside the chamber to outside the chamber.

35. The method of claim 33, wherein the distal end of the micro-element includes an exposed portion outside of the wall of the shell.

36. The method of claim 33, wherein the micro-element includes a micro-electrode element at its distal end and the at least one wire is attached to the micro-electrode element.

37. The method of claim 33, wherein the micro-element has at least two wires adapted for temperature sensing.

38. The method of claim 33, further comprising a plurality of micro-elements each having a distal end, wherein the distal ends of the micro-elements are arranged in a radial pattern in the distal portion of the electrode about a longitudinal axis of the electrode.

* * * * *